United States Patent
Howell et al.

(10) Patent No.: US 10,682,462 B2
(45) Date of Patent: Jun. 16, 2020

(54) SEPARATABLE INFUSION SET WITH CLEANABLE INTERFACE AND STRAIGHT LINE ATTACHMENT

(75) Inventors: Glade H. Howell, Sandy, UT (US); Weston F. Harding, Lehi, UT (US); Bart D. Peterson, Farmington, UT (US); Christopher N. Cindrich, Draper, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1422 days.

(21) Appl. No.: 12/736,678

(22) PCT Filed: May 13, 2009
(Under 37 CFR 1.47)

(86) PCT No.: PCT/US2009/002947
§ 371 (c)(1),
(2), (4) Date: Mar. 14, 2011

(87) PCT Pub. No.: WO2009/139857
PCT Pub. Date: Nov. 19, 2009

(65) Prior Publication Data
US 2011/0213340 A1 Sep. 1, 2011

Related U.S. Application Data

(60) Provisional application No. 61/071,713, filed on May 14, 2008.

(51) Int. Cl.
*A61M 5/158* (2006.01)

(52) U.S. Cl.
CPC ...... *A61M 5/158* (2013.01); *A61M 2005/1581* (2013.01); *A61M 2005/1587* (2013.01)

(58) Field of Classification Search
CPC .. A61M 2005/1581; A61M 2005/1587; A61M 2005/14252; A61M 2005/1585;
(Continued)

(56) References Cited

U.S. PATENT DOCUMENTS

| 3,918,355 A | 11/1975 | Weber |
| 4,490,141 A | 12/1984 | Lacko et al. |

(Continued)

FOREIGN PATENT DOCUMENTS

| CA | 2653568 | * 12/2007 |
| EP | 1096968 | 5/2001 |

(Continued)

*Primary Examiner* — Bhisma Mehta
*Assistant Examiner* — Laura C Schell
(74) *Attorney, Agent, or Firm* — Dickinson Wright PLLC

(57) ABSTRACT

Infusion sets for insertion into an insertion site for preventing misalignment of the base and cap or fluid connector by providing one or more alignment features between each, and in alternative embodiments, provide one or more features to secure the cap or fluid connector to the base in anyone of a number of rotational positions and having release features to allow the cap or fluid connector to be rotatable with respect to the base portion of the infusion set, and yet easily removed and inserted. Further embodiments provide infusion sets wherein the user can easily see the insertion site of the catheter and the skin, to determine if infections have occurred at an earlier stage than was possible using prior art infusion sets and with substantially less difficulty.

21 Claims, 30 Drawing Sheets

(58) Field of Classification Search
CPC ........... A61M 2005/1586; A61M 2005/14256; A61M 2005/1426; A61M 2005/14284; A61M 5/158–2005/1588; A61M 5/3287–349; A61M 25/02–0693; A61M 5/32–3219
USPC .................. 604/533, 534, 535, 536
See application file for complete search history.

(56) References Cited

U.S. PATENT DOCUMENTS

| | | | |
|---|---|---|---|
| 5,186,712 A * | 2/1993 | Kelso | A61M 25/0606 604/157 |
| 5,195,985 A | 3/1993 | Hall | |
| 5,312,364 A * | 5/1994 | Jacobs | A61B 17/3472 604/174 |
| 5,423,775 A * | 6/1995 | Cannon | A61M 39/1011 285/305 |
| 5,507,733 A * | 4/1996 | Larkin | A61M 39/045 285/322 |
| 5,545,152 A | 8/1996 | Funderburk et al. | |
| 5,814,020 A * | 9/1998 | Gross | A61M 5/14248 604/141 |
| 5,851,197 A * | 12/1998 | Marano | A61M 5/158 604/135 |
| 6,007,516 A * | 12/1999 | Burbank et al. | 604/288.03 |
| 6,248,093 B1 | 6/2001 | Moberg | |
| 6,530,900 B1 * | 3/2003 | Daily | A61M 5/14248 604/132 |
| 6,585,695 B1 | 7/2003 | Adair et al. | |
| 6,830,562 B2 * | 12/2004 | Mogensen et al. | 604/164.12 |
| 7,350,764 B2 * | 4/2008 | Raybuck | 251/149.1 |
| 7,390,314 B2 | 6/2008 | Stutz, Jr. et al. | |
| 7,628,772 B2 | 12/2009 | McConnell et al. | |
| 7,628,782 B2 | 12/2009 | Adair et al. | |
| 7,658,734 B2 | 2/2010 | Adair et al. | |
| 7,686,787 B2 | 3/2010 | Moberg et al. | |
| 7,713,258 B2 | 5/2010 | Adams et al. | |
| 8,172,803 B2 | 5/2012 | Morrissey et al. | |
| 8,221,359 B2 | 7/2012 | Kristensen et al. | |
| 8,262,618 B2 | 9/2012 | Scheurer | |
| 8,277,415 B2 | 10/2012 | Mounce et al. | |
| 8,285,328 B2 | 10/2012 | Caffey et al. | |
| 8,287,467 B2 | 10/2012 | List et al. | |
| 8,287,516 B2 | 10/2012 | Kornerup et al. | |
| 8,306,596 B2 | 11/2012 | Schurman et al. | |
| 8,310,415 B2 | 11/2012 | McLaughlin et al. | |
| 8,313,468 B2 | 11/2012 | Geipel et al. | |
| 2001/0025168 A1 * | 9/2001 | Gross | A61M 5/14248 604/506 |
| 2002/0123724 A1 * | 9/2002 | Douglas et al. | 604/177 |
| 2002/0173748 A1 | 11/2002 | McConnell et al. | |
| 2003/0176852 A1 * | 9/2003 | Lynch | A61M 5/14244 604/890.1 |
| 2004/0003493 A1 | 1/2004 | Adair et al. | |
| 2004/0044306 A1 | 3/2004 | Lynch et al. | |
| 2004/0158207 A1 | 8/2004 | Hunn et al. | |
| 2005/0020972 A1 * | 1/2005 | Horisberger | A61M 5/158 604/93.01 |
| 2005/0101912 A1 | 5/2005 | Faust et al. | |
| 2006/0001551 A1 | 1/2006 | Kraft et al. | |
| 2006/0106349 A1 * | 5/2006 | Kito et al. | 604/187 |
| 2006/0173410 A1 | 8/2006 | Moberg et al. | |
| 2007/0078393 A1 | 4/2007 | Lynch et al. | |
| 2007/0093754 A1 | 4/2007 | Mogensen et al. | |
| 2007/0185454 A1 * | 8/2007 | Fangrow, Jr. | A61M 5/158 604/164.01 |
| 2007/0219496 A1 * | 9/2007 | Kamen | G05D 7/0647 604/131 |
| 2008/0103483 A1 | 5/2008 | Johnson et al. | |
| 2008/0319414 A1 | 12/2008 | Yodfat et al. | |
| 2009/0012472 A1 | 1/2009 | Ahm et al. | |
| 2009/0137979 A1 | 5/2009 | Adair et al. | |
| 2009/0198191 A1 | 8/2009 | Chong et al. | |
| 2009/0198215 A1 | 8/2009 | Chong et al. | |
| 2009/0221971 A1 * | 9/2009 | Mejlhede | A61M 5/142 604/180 |
| 2009/0240240 A1 | 9/2009 | Hines et al. | |
| 2009/0254041 A1 | 10/2009 | Krag et al. | |
| 2009/0259183 A1 | 10/2009 | Chong et al. | |
| 2009/0259198 A1 | 10/2009 | Chong et al. | |
| 2009/0259209 A1 | 10/2009 | Chong et al. | |
| 2009/0326457 A1 | 12/2009 | O'Connor | |
| 2010/0049129 A1 | 2/2010 | Yokoi et al. | |
| 2010/0049135 A1 | 2/2010 | Adair et al. | |
| 2010/0049144 A1 | 2/2010 | McConnell et al. | |
| 2010/0082010 A1 | 4/2010 | Adair et al. | |
| 2010/0160902 A1 | 6/2010 | Aeschlimann et al. | |
| 2010/0286714 A1 | 11/2010 | Gyrn et al. | |
| 2010/0291588 A1 | 11/2010 | McDevitt et al. | |
| 2010/0298830 A1 | 11/2010 | Browne et al. | |
| 2012/0253282 A1 | 10/2012 | Nagel et al. | |
| 2012/0259185 A1 | 10/2012 | Yodfat et al. | |
| 2012/0265034 A1 | 10/2012 | Wisniewski et al. | |
| 2012/0277554 A1 | 11/2012 | Schurman et al. | |
| 2012/0277667 A1 | 11/2012 | Yodat et al. | |
| 2012/0277724 A1 | 11/2012 | Larsen et al. | |
| 2012/0283540 A1 | 11/2012 | Brüggemann | |
| 2012/0291778 A1 | 11/2012 | Nagel et al. | |
| 2012/0293328 A1 | 11/2012 | Blomquist | |
| 2012/0296269 A1 | 11/2012 | Blomquist | |
| 2012/0296310 A1 | 11/2012 | Blomquist | |
| 2012/0296311 A1 | 11/2012 | Brauker et al. | |

FOREIGN PATENT DOCUMENTS

| | | |
|---|---|---|
| JP | 2007-511325 A | 5/2007 |
| WO | WO-00/03757 A1 | 1/2000 |
| WO | WO 2004-091692 A2 | 10/2004 |
| WO | WO 2005-049117 A2 | 6/2005 |

* cited by examiner

US 10,682,462 B2

SEPARATABLE INFUSION SET WITH CLEANABLE INTERFACE AND STRAIGHT LINE ATTACHMENT

CROSS-REFERENCE TO RELATED APPLICATIONS

This application claims benefit under 35 U.S.C. § 119(e) of U.S. Provisional Patent Application No. 61/071,713, entitled "A Separatable Infusion Set With Cleanable Interface and a Straight Line Attachment", filed May 14, 2008, the entire content of which is expressly incorporated herein by reference.

BACKGROUND OF THE INVENTION

1. Field of the Invention

The present invention relates to infusion sets. More particularly, the present invention relates to an infusion set that provides a self sealing septum so that a user can remove a cap with extension tubing without introducing foreign substances into the body through the catheter assembly. Further, the present invention relates to an infusion set wherein the cap assembly portion can rotate so that the extension tubing, which provides the liquid medication to the user from an infusion pump or the like, can be conveniently located and changed at any time by the user.

2. Description of the Related Art

At the most basic level, whenever a liquid medication is to be delivered into or through the skin of a patient from an external source, a hollow needle or other type of cannula or catheter device must first be inserted in order to provide a passageway or channel through which the fluid may pass. Once this passageway has been provided, any suitable infusion set or system may be used in conjunction with an appropriate tube or conduit connecting the external source of liquid with the passageway leading to the subcutaneous delivery point to deliver the liquid to the patient at an appropriate delivery rate.

One class of devices that can be used to deliver liquid medications into or through the skin of a patient are known as infusion sets. FIG. 1 illustrates the components of a known infusion set 250. Infusion sets 250 generally comprise a relatively short cannula or catheter 256 that is supported by and protrudes from a compact housing 260 adapted to receive the infusion fluid via a delivery tube 252 connected suitably to other components of a fluid infusion system. For optimum patient comfort during use, the cannula 256 is desirably constructed with a high degree of softness and flexibility. The infusion set 250 can also include a liquid pump 251, among other devices. An insertion needle 253 is normally provided to extend through a lumen formed in the cannula 256 to facilitate placement of the cannula 256, either into or through the skin, after which the insertion needle 253 is withdrawn to leave the cannula 256 in place for fluid infusion into the patient.

The housing 260 itself can comprise a cap or fluid connector 254 and a base 255 that are separable. The base 255 is attached to the patient's skin during cannula insertion and the cap 254 is attached to the base 255 after the insertion needle 253 is removed. The base 255 is attached to the patient by an attachment means, generally an adhesive pad 257 that provides sufficient adhesion to the skin to keep the housing 260 in place for several days, but not too much adhesion to cause damage to the patient's skin.

The base 255 may also include a septum 258 that provides a self-sealing interface. This interface is necessary because the insertion needle 253 is used to put the cannula 256 in place, as discussed above. The insertion needle 253 extends through the septum 258 into the cannula 256 for cannula placement. After the insertion needle 253 is removed and replaced with the cap 254, liquid flows through the delivery tube 252 into an interior chamber 259 of the base 255 via the cap 254. The septum 258 seals the chamber 259 from the exterior environment after the insertion needle 253 has inserted the cannula 256 and has been removed. The liquid enters the chamber 259 and then the patient through cannula 256.

Unfortunately, many problems exist with the infusion sets of the prior art. For example, prior art infusion sets 250 are difficult to assemble once the catheter 256 has been inserted into the body. In some prior art infusion sets 250, it is difficult to align the cap 254 and base 255 of the infusion set 250. Therefore, after cleaning an insertion site, it is difficult to assemble the infusion set 250 so that it works properly. Often, the infusion sets 250 of the prior art are unidirectional, by which it is meant that the direction of the extension tubing 252 with respect to the base 255 of the infusion set 250 is fixed and cannot be changed once the infusion set 250 has been inserted and attached to the skin of the user. Additionally, in some prior art infusion sets, it is difficult to ensure a good seal between the septum 258 and the fluid path, and occasionally fluids leak because of this poor seal. Furthermore, in many prior art infusion sets 250 it is difficult to mate the cap 254 and base 255 of the infusion set 250 even if proper alignment can be obtained.

Other difficulties are present in the infusion sets of the prior art that relate to the position of the insertion site. In the prior art infusion sets 250, the insertion site is located below the base 255, and therefore cannot be seen by the user after insertion. Often, infections can occur, which generally are indicated by a slight reddening of the insertion site, followed by soreness and possible other signs of infection. Also, in many infusion sets of the prior art, once alignment and mating are achieved, the cap 254 is difficult to remove and re-attach to the base 255 of the infusion set 250.

It is therefore desirable to provide an infusion set that overcomes these and other difficulties associated with the infusion sets of the prior art.

SUMMARY OF THE INVENTION

Accordingly, it is an object of at least a first embodiment of the present invention to substantially solve these and other problems associated with the prior art and to do so, provide at least an infusion set that does not require any rotational alignment when connecting the cap to the base. In an exemplary embodiment of the present invention, the cap of the infusion set is configured to rotate freely about the base once the two are attached together, so the extension tube can be rotated to any desired orientation. Further, the infusion set according to the first exemplary embodiment of the present invention can provide ribs on both a post of the base and a retention member of the cap which interlock, allowing the user to lock the cap at any desired angular position, or to change to a new position from an initial position. In doing so, exemplary embodiments of the present invention can provide a low-profile, easily cleanable device, that can be easily assembled in any position, yet provide rotation restriction where desired.

It is a further object of at least the first embodiment of the present invention to provide at least an infusion set that allows the user to connect the cap to the base with a straight-down motion orthogonal to the body, and without having to manipulate any buttons or levers to complete the connection. Further, the infusion set according to the first exemplary embodiment of the present invention can provide a retention means that enables the cap and base to automatically be locked together. This substantially eliminates the chance of dislodging the catheter with any sideways or twisting forces and substantially simplifies the connection process for the user. Furthermore, the infusion set according to the first exemplary embodiment of the present invention can provide a post of the base and corresponding retention means lead-ins of the post and/or the cap that allow easy alignment between the base and cap of the infusion set by the user.

It is another object of at least the first embodiment of the present invention to provide at least an infusion set with angular lead-ins on the post and retention means, so that a user can substantially misalign the cap and base and yet still substantially easily connect the two, as the two self-align for the final connection. Further, because of the inherent symmetry of the cap and the base, a particular orientation is not necessary when aligning the cap and base.

It is therefore another object of at least the first embodiment of the present invention to provide at least an infusion set with concentric circles on the cap and the base that have generous lead-ins that guide the cap and base together, thereby permitting easier alignment between the two.

It is an object of at least a second embodiment of the present invention to provide an infusion set in which a blunt cannula can be introduced through the septum from the top of the septum that substantially eliminates the possibility of contamination and infection.

It is another object of at least the second embodiment of the present invention to provide at least an infusion set having a rotational interlocking means for connecting the fluid cap to the base. It is a further object of the second exemplary embodiment of the present invention to provide at least an infusion set having a latching interlocking means for securing the fluid cap to the base and for subsequently releasing the fluid cap from the base.

It is another object of at least the second embodiment of the present invention to provide an infusion set that permits a user to connect the cap to the base in a straight-down motion, orthogonal to the body, and without having to manipulate buttons or levers to complete the connection. It is a further object of the second exemplary embodiment of the present invention to provide an infusion set with a retention means that automatically locks the cap to the base, thereby substantially eliminating any chance of dislodging the catheter with sideways or twisting forces. This simplifies the connection process for the user.

It is an object of at least a third embodiment of the present invention to provide a window arrangement for use in an infusion set to afford the user with the ability to view the needle insertion site. Such a window arrangement gives the user of the infusion set the opportunity to keep the insertion site of the infusion set cleaner and more sterile, by allowing the user to treat an incipient infection or irritation at the first sign.

It is a further object of at least the third embodiment of the present invention to provide an infusion set that allows the user to monitor the insertion sites for infections or irritations. Accordingly, it is an object of the third exemplary embodiment to provide a lens arrangement that comprises one or both of a clear flat lens or a clear magnified lens. Further, these lenses can be made of any suitable material, including, but not limited to, plastic and glass, among other materials.

It is an object of at least a fourth embodiment of the present invention to provide a septum holding device for use in the infusion set according to the embodiments of the present invention such that the septum is not free to become dislodged, and remains substantially fixed in location even after numerous insertions of a blunt cannula. It is a further object of the fourth exemplary embodiment of the present invention to provide an infusion set in which a secondary part is not necessary to hold the septum in place, therefore reducing part inventory and manufacturing costs. In each embodiment, the exemplary septum can be easily sterilized prior to positioning (i.e., at insertion or re-insertion) in the device, and can thereafter be cleaned prior to insertion or re-insertion of the blunt cannula to further reduce the risk of infection.

It is an object of at least fifth through eleventh embodiments of the present invention to provide at least an infusion set having a cap retention means for use in infusion sets. The cap retention means according to the fifth through eleventh exemplary embodiments of the present invention permits an easier connection between the cap and the base than the infusion sets of the prior art.

It is also an object of at least the fifth through eleventh embodiments of the present invention to provide a cap retention means for use in an infusion set, wherein the cap retention means does not require rotational alignment when connecting the cap to the base.

It is a further object of at least the fifth through eleventh embodiments of the present invention to provide a cap retention means for use in an infusion set wherein the cap retention means allows the cap to rotate freely once attached so that the extension tube can be rotated to any desired orientation.

It is a further object of at least the fifth embodiment of the present invention to provide at least an infusion set having a cap retention means that comprises a flexible cap wherein a user compresses two sides together, forcing two other sides to bow outwardly, allowing placement of the cap over the base, at any desired orientation of the infusion set.

It is an object of at least the sixth embodiment of the present invention to provide at least an infusion set having a cap retention means that comprises a flexible cap wherein a user compresses a wedge into an opening formed by a flexible cap holder with three sides, and wherein after placement of the wedge, two other sides bow outwardly, allowing placement of the cap over the base, at any desired orientation of the infusion set.

It is an object of at least the seventh embodiment of the present invention to provide at least an infusion set having a cap retention means that comprises a flexible cap wherein a user compresses at least one or more levers together, forcing the flexible cap to flex a circular retention means away from a base wall, thereby releasing the flexible cap from the base. It is a further object of at least the seventh embodiment of the present invention to provide a flexible cap wherein the user also compresses at least one or more levers together, forcing the flexible cap to flex a circular retention means outwardly, allowing placement of the cap over the base, as the circular retention means interfaces with the base wall upon release of the levers.

It is an object of at least the eighth embodiment of the present invention to provide at least an infusion set having a cap retention means that comprises a rigid hoop wherein a user compresses one side of the rigid hoop against a spring to release the cap from the base by moving a second rigid hoop extension/retention member located at a first end of the cap from under an undercut formed on a post on the base of the infusion set. The user can then lift the first end of the cap up and then the second end of the cap, located distally from the first end, releasing the cap from the base.

It is an object of at least the ninth embodiment of the present invention to provide at least an infusion set having a cap retention means that comprises a cap wherein a user compresses at least one or more levers, that can be spring-loaded, about a pivot, to either retain the cap to the base by the lever arm locking under an undercut formed on the post on the base, or release it therefrom.

It is an object of at least the tenth embodiment of the present invention to provide at least an infusion set having a cap retention means that comprises a cap wherein a user compresses a spring retention member that interfaces with an undercut of a cap retaining wall that is on the base of the infusion set to either retain the cap to the base, or release it therefrom.

It is an object of at least the eleventh embodiment of the present invention to provide at least an infusion set having a cap retention means that comprises a cap wherein a user moves a spring retention lever that interfaces with an undercut of a cap retaining wall that is on the base of the infusion set to either retain the cap to the base, or release it therefrom.

BRIEF DESCRIPTION OF THE DRAWINGS

The various objects, advantages and novel features of the present invention will be best understood by reference to the detailed description of the preferred embodiments which follows, when read in conjunction with the accompanying drawings, in which.

DETAILED DESCRIPTION OF THE EXEMPLARY EMBODIMENTS

Figure 1:
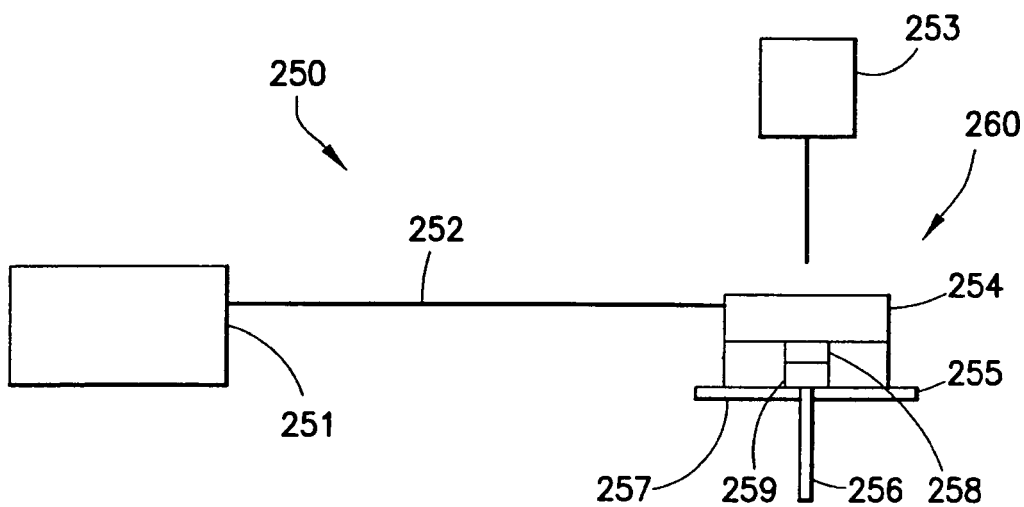
FIG. 1 illustrates a conventional infusion set according to the prior art.

Several embodiments of the present invention will now be described in detail with reference to the annexed drawings. In the drawings, the same or similar elements are denoted by the same reference numerals even though they are depicted in different drawings.

Referring to FIGS. 2-9, an exemplary infusion set 100 according to a first embodiment of the present invention is shown in various views. The infusion set 100 according to first embodiment of the present invention comprises a catheter 2, a self sealing separatable junction, an extension tubing 6 and a pump 46.

As shown in FIGS. 2A, 2B, 2D, 4A, 4B, 5A, and 5B, the self sealing separatable junction comprises a base 4 that has a post 8 with an undercut 10, the catheter 2 and a septum 12 to seal the proximal end of the catheter 2. As shown in FIGS. 2A, 2B, 2D, 3A-3E, 5A, and 5D, a cap 14 includes a tube or opening 16, a retention member 18, a method of releasing the retention member 18 (not shown), a blunt cannula and blunt cannula cover 20 and the extension tubing 6 with luer connector (also not shown).

Figure 2A:
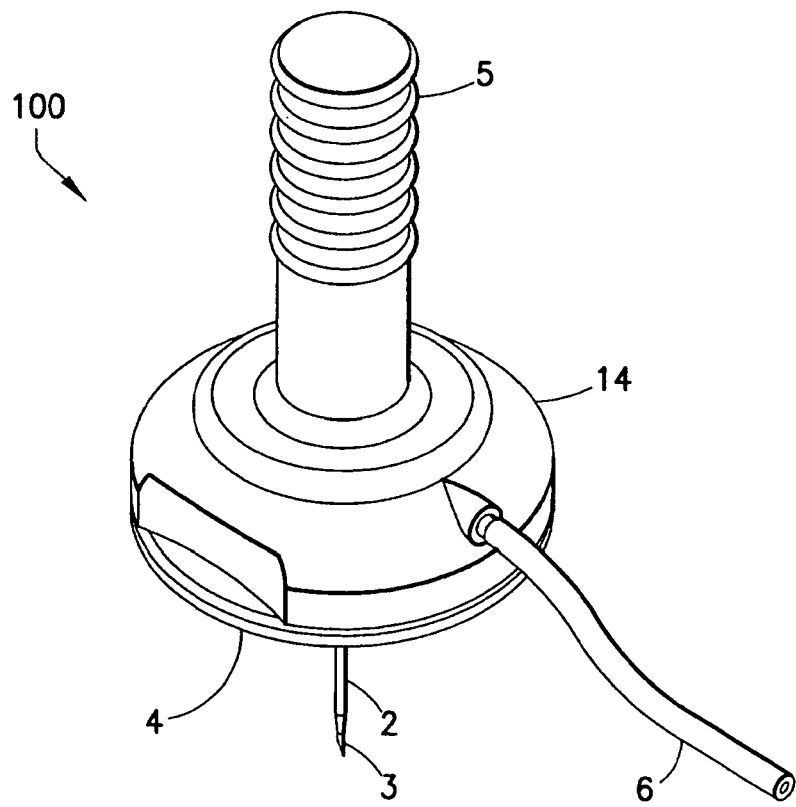
FIG. 2A is an isometric view of an infusion set in a pre-insertion state with a needle hub assembly according to a first embodiment of the present invention.
Figure 2B:
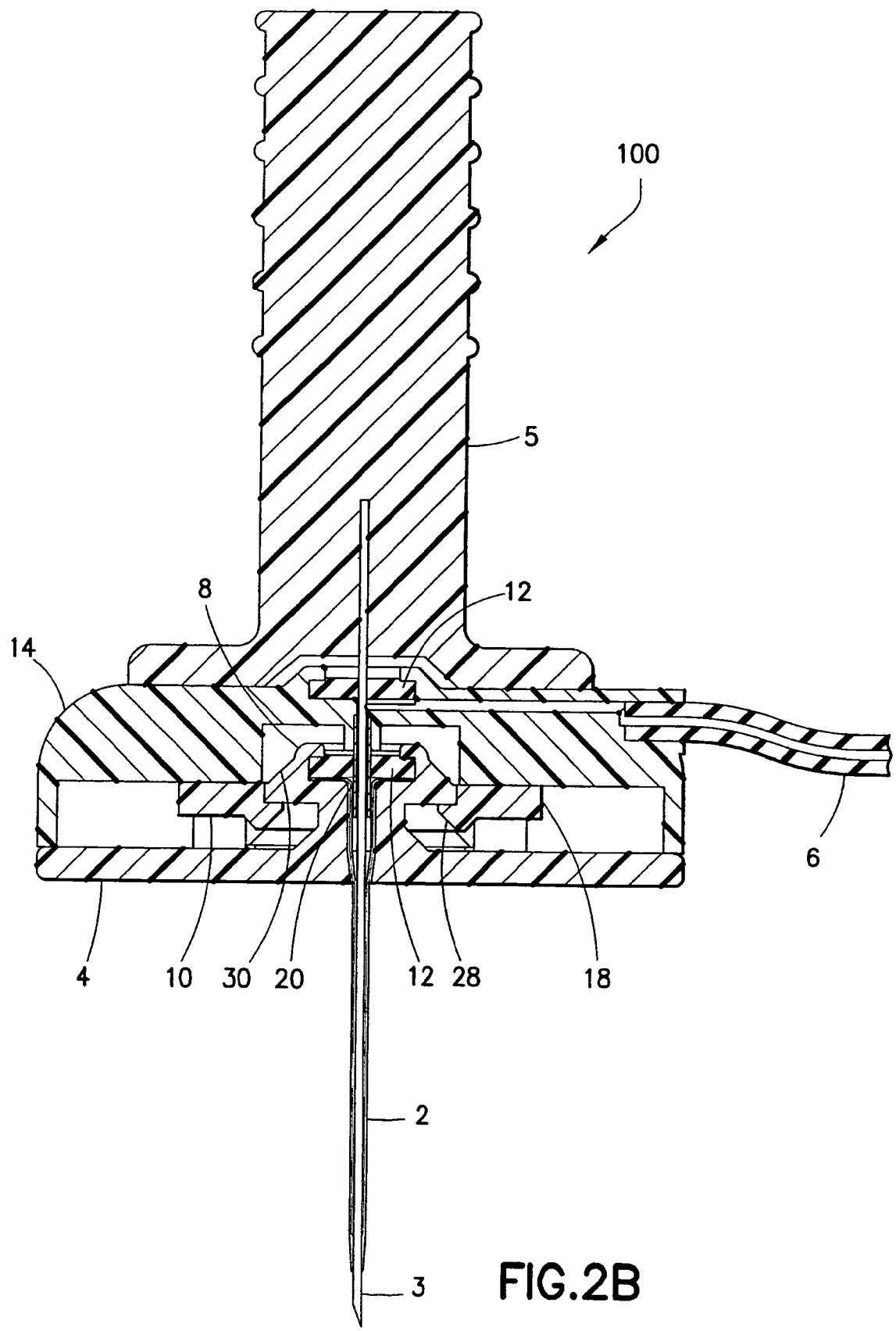
FIG. 2B is a cross-sectional view of the infusion set shown in FIG. 2A.
Figure 2C:
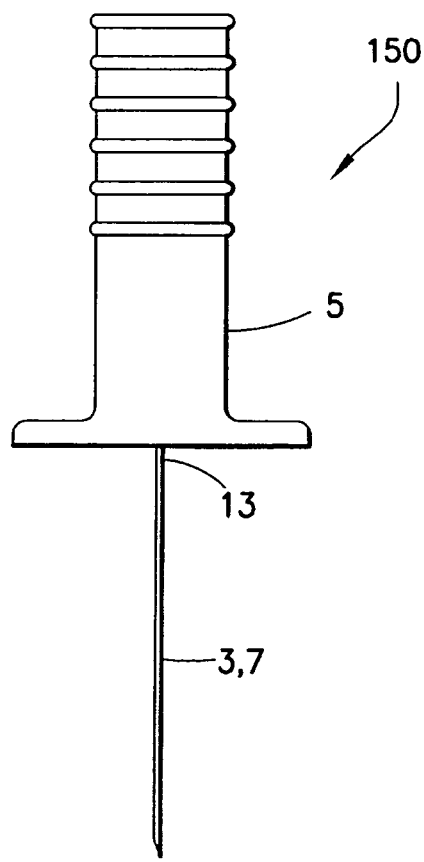
FIG. 2C is a side view of the needle hub assembly shown in FIG. 2A.
Figure 2D:
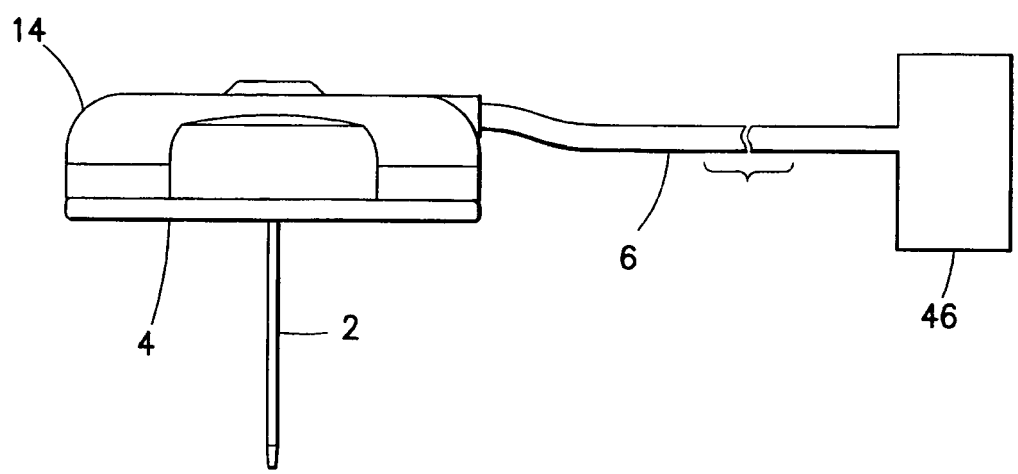
FIG. 2D is a side view of the infusion set shown in FIG. 2A in a post-insertion state with a fluid delivery pump assembly.
Figure 2E:
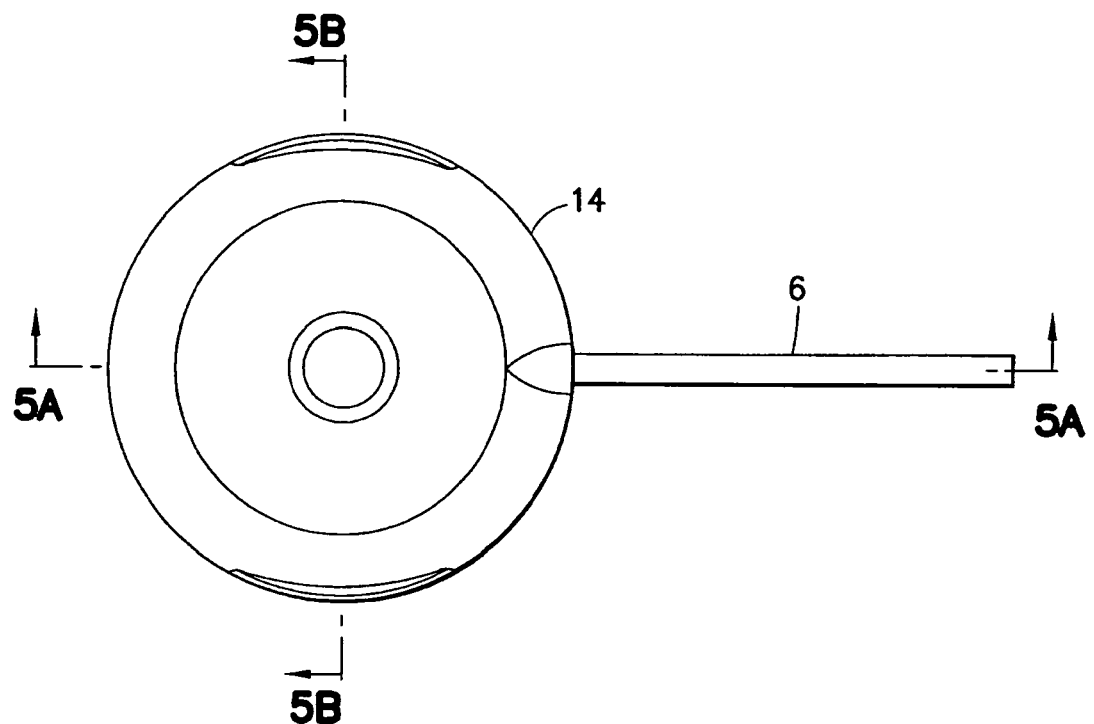
FIG. 2E is a top view of the infusion set shown in FIG. 2A.
Figure 3A:
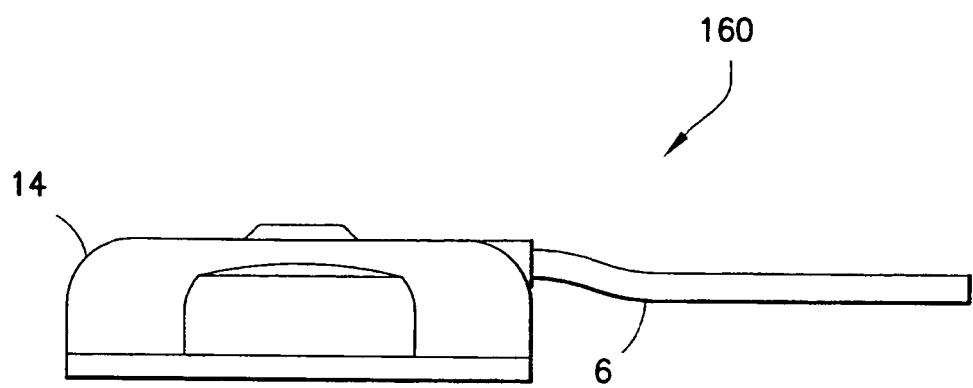
FIG. 3A is a side view of an exemplary tubing set connector assembly for use with the infusion set shown in FIG. 2A in accordance with an embodiment of the present invention.
Figure 3B:
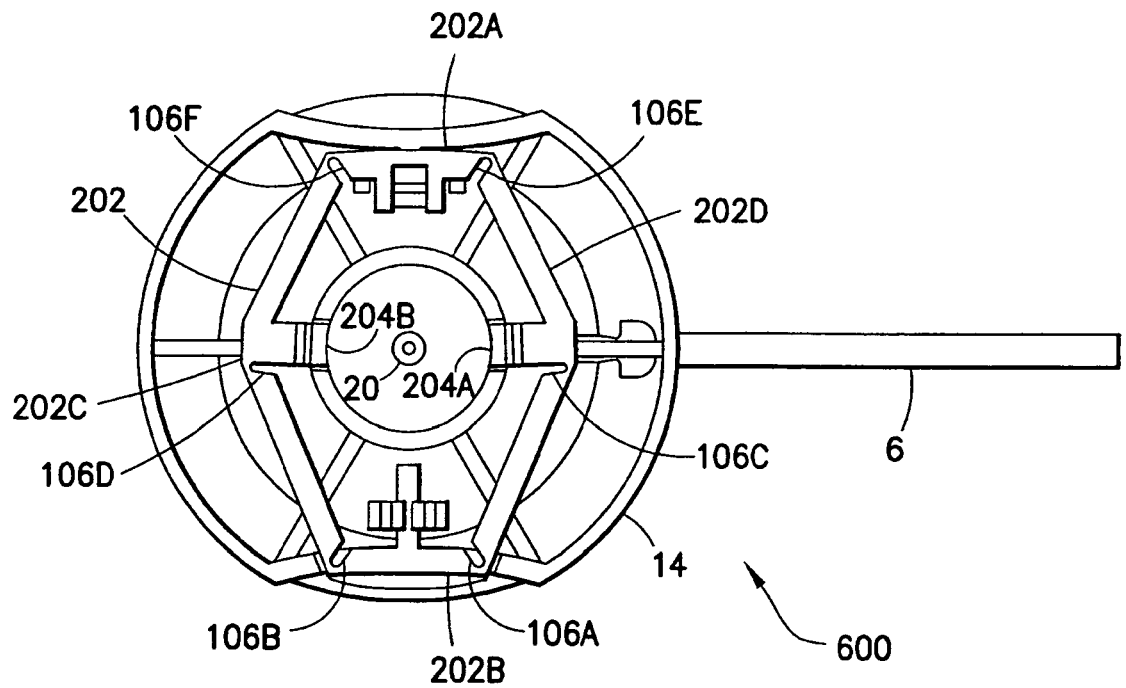
FIG. 3B is a bottom view of the tubing set connector shown in FIG. 3A with a latching mechanism open in accordance with an embodiment of the present invention.
Figure 3C:
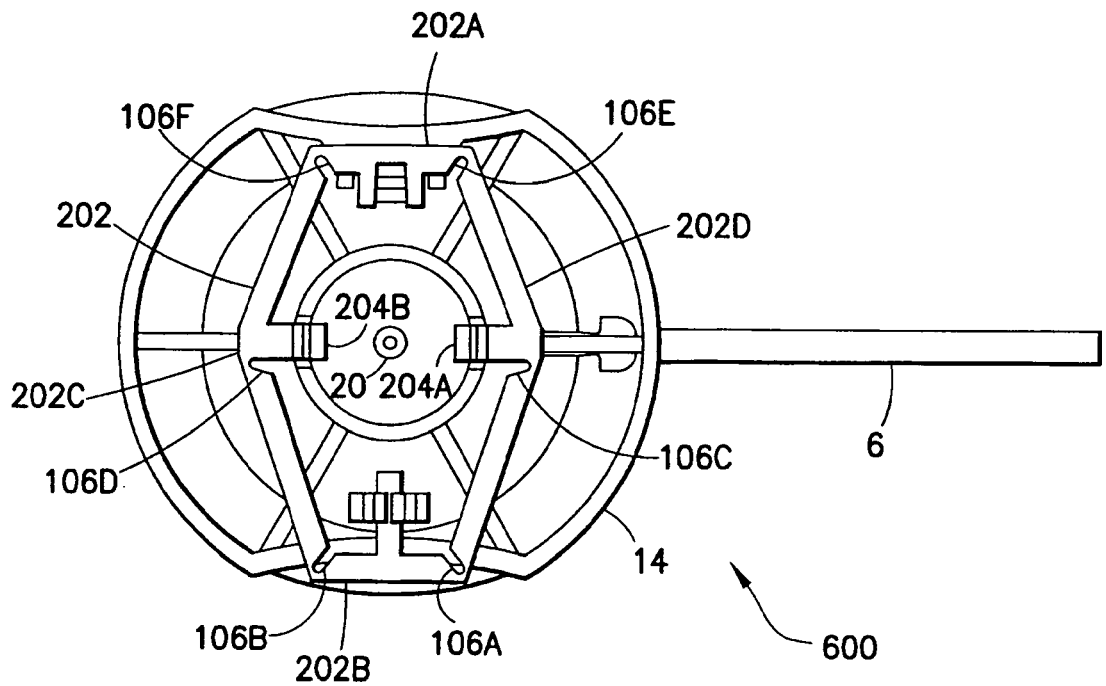
FIG. 3C is a bottom view of the tubing set connector shown in FIG. 3A with the latching mechanism closed in accordance with an embodiment of the present invention.
Figure 3D:
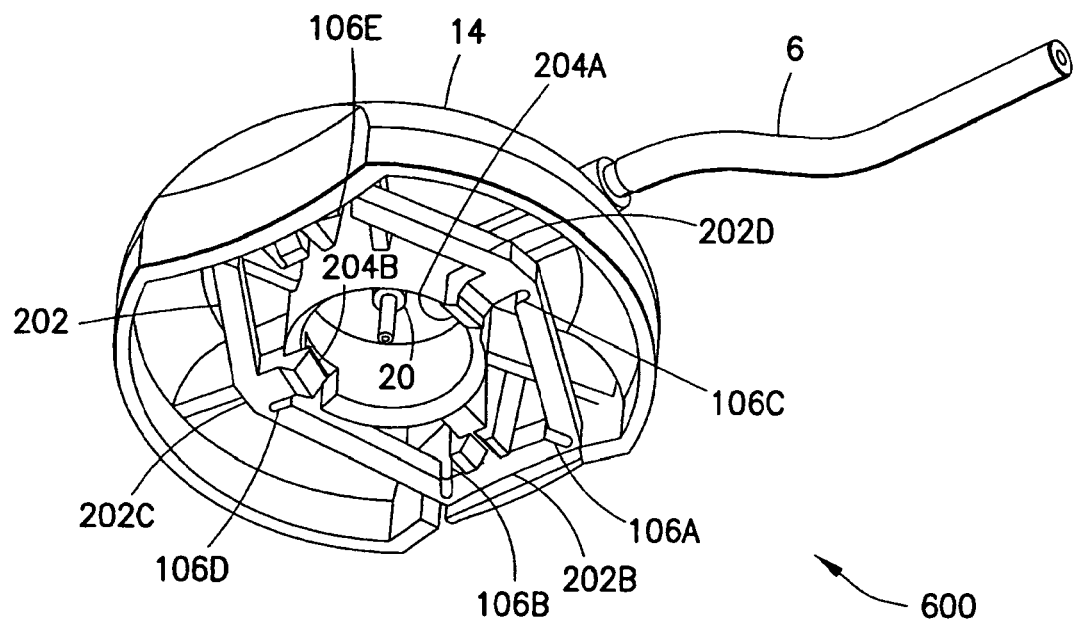
FIG. 3D is a bottom isometric view of the tubing set connector shown in FIG. 3A with the latching mechanism open in accordance with an embodiment of the present invention.
Figure 3E:
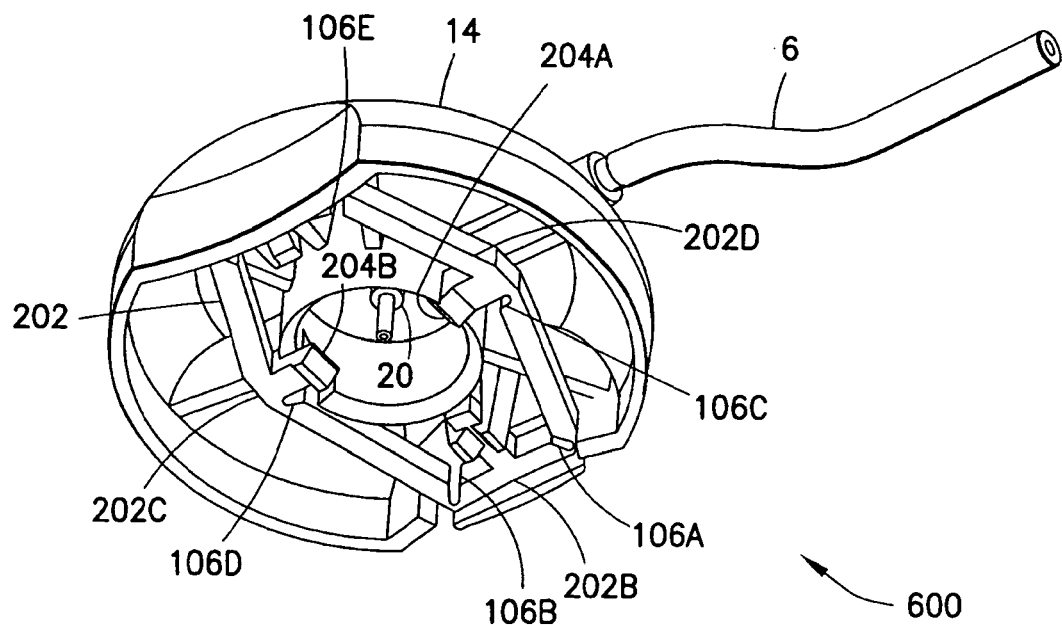
FIG. 3E is a bottom isometric view of the tubing set connector shown in FIG. 3A with the latching mechanism closed in accordance with an embodiment of the present invention.

FIGS. 2A, 2B and 2C illustrate a needle hub assembly 150 used in at least the first and second embodiments of the present invention. The needle hub assembly 150 comprises a needle grip 5, and an insertion needle 3. Alternatively, the needle hub assembly can use other needles, such as the exemplary insertion needle 7 (see FIG. 9), which is a hollow needle that has one or more holes 13 configured to perform one or more additional functions as desired (see FIG. 9, discussed in greater detail below).

The needle hub assembly 150 is used to insert the catheter 2 of the infusion set 100, 200 into the body of a user so that the catheter 2 does not bend or crumple, and is positioned at the correct depth for delivery of the user's medication via the infusion set 100, 200. To insert the catheter 2 into the skin of the user, the user grips the needle grip 5 and inserts the needle 3, 7 through the septum 12 of the infusion set 100, 200. The stiffened catheter 2, with the needle 3, 7 can then be inserted into the skin of the user, and the infusion set 100, 200 can then be affixed to the user's skin with an adhesive patch located on the bottom of the base 4 of the infusion set 100, 200.

FIGS. 3A-3E illustrate several views of an exemplary tubing set connector assembly 160 that can comprise the cap 14, attached tubing 6, and an exemplary latching mechanism in accordance with an embodiment of the present invention. In FIGS. 3B-3E, a latching mechanism 600 is illustrated as a means to fix the cap 14 onto the base 4 of the infusion set 100. This latching mechanism 600 will be described in greater detail below in reference to FIGS. 20A and 20B.

Figure 4A:
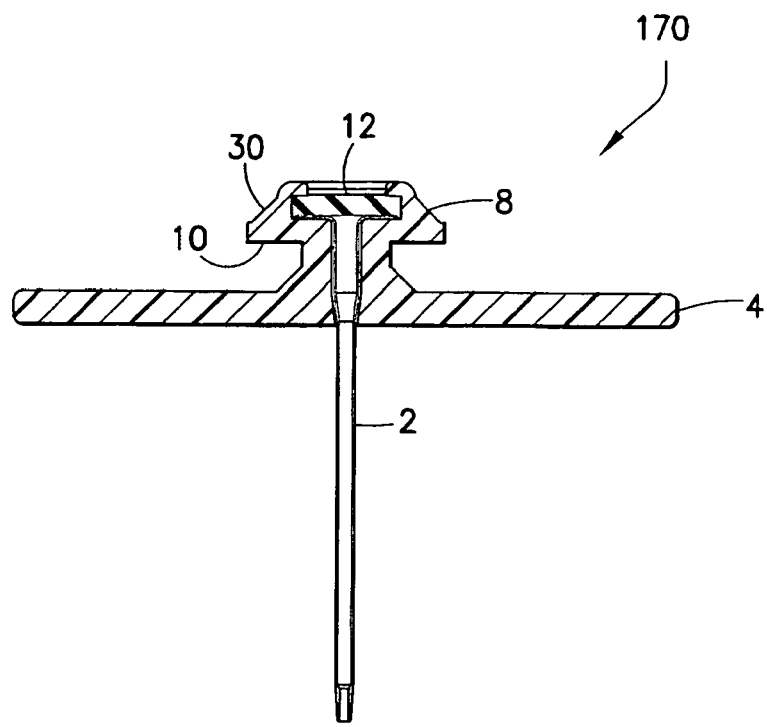
FIG. 4A is a cross-sectional view of a catheter and connection port assembly for use with the infusion set shown in FIG. 2A in accordance with an embodiment of the present invention.
Figure 4B:
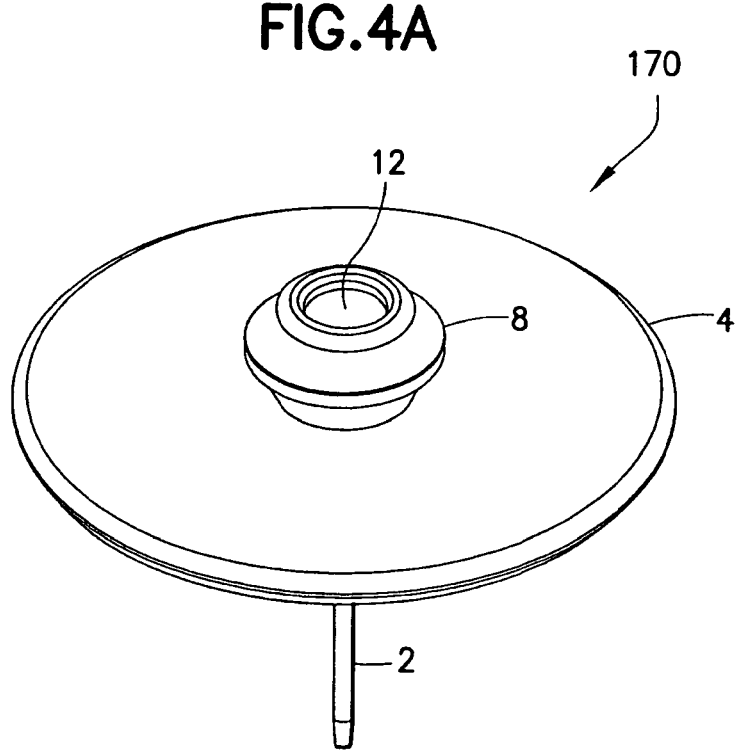
FIG. 4B is a top isometric view of the catheter and connection port assembly shown in FIG. 4A in accordance with an embodiment of the present invention.

FIGS. 4A and 4B illustrate cross-sectional and isometric views of a connection port assembly 170. The connection port assembly comprises the base 4 and post 8. The post 8 can comprise a substantially cylindrical member extending perpendicular from a substantially flat base 4, but is not limited thereto. As shown in FIG. 4A, the post and base can be formed as one piece, and the post 8 can be further configured to provide a detent, shoulder, or other similarly functioning undercut 10 which can be releasably captured by one or more members provided on the cap (not yet shown), and can further be configured to provide a post lead-in surface 30. The undercut 10 and post lead-in 30 can be used to facilitate the excellent alignment and/or latching features of the infusion sets 100, 200, and are each described in greater detail below.

Figure 5A:
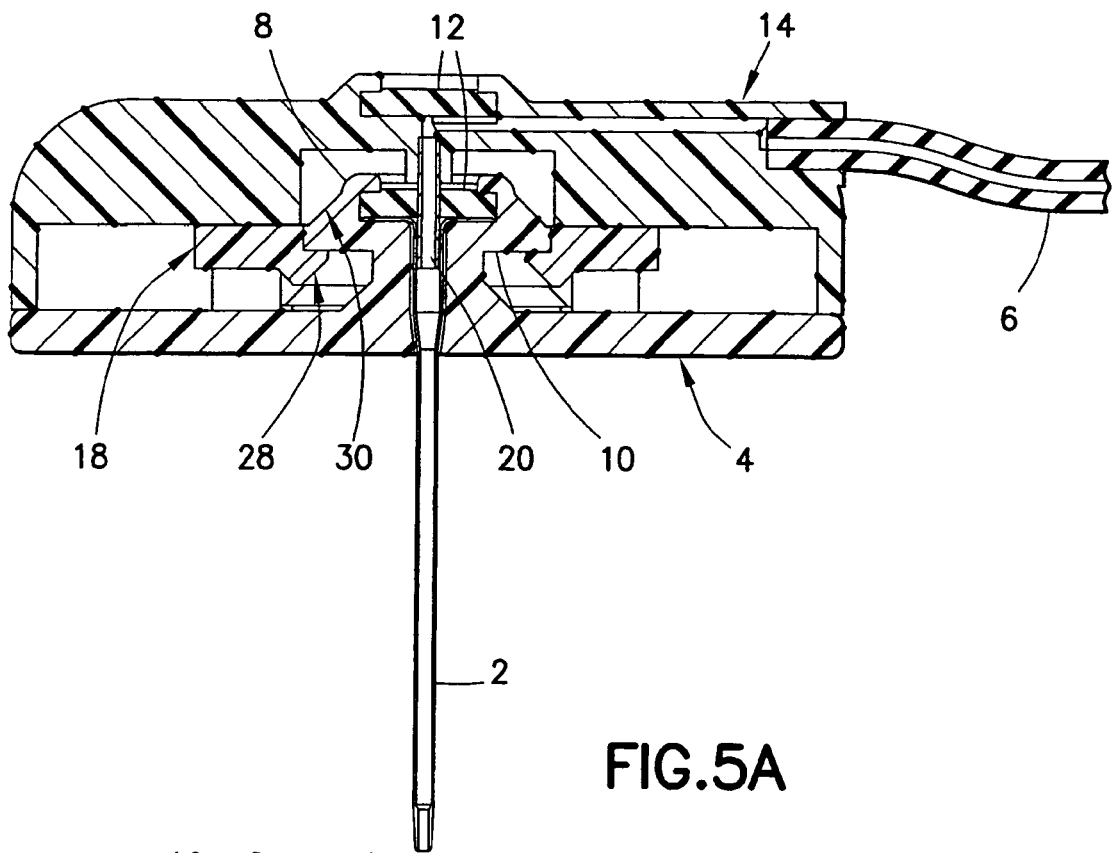
FIG. 5A is a cross-sectional view of the infusion set as shown in FIG. 2E along the lines 5A-5A.
Figure 5B:
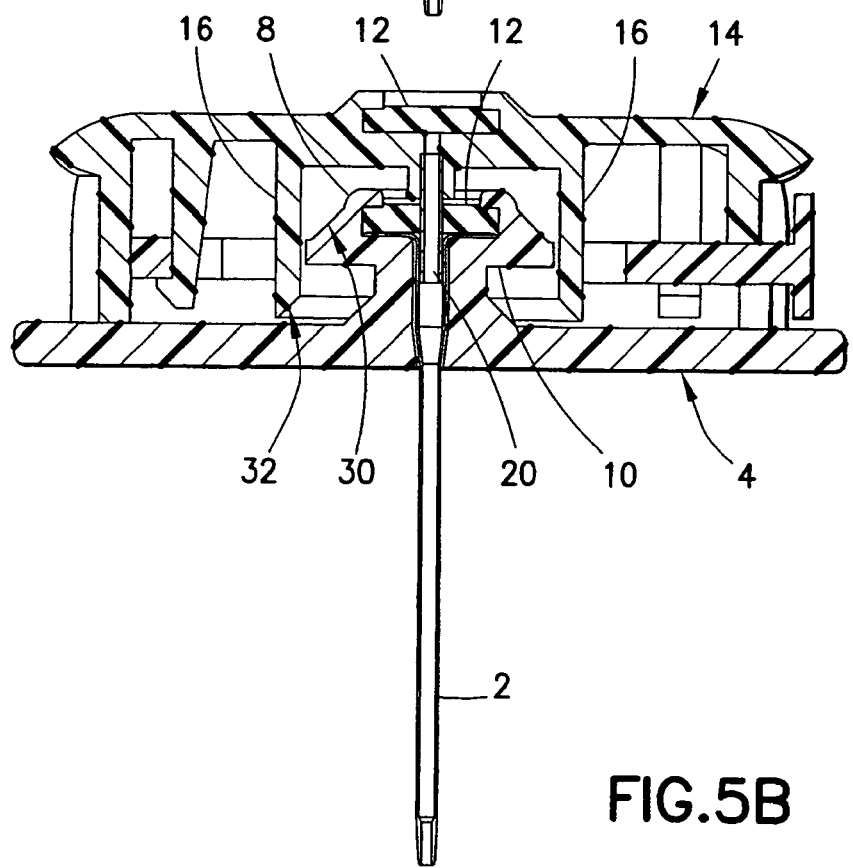
FIG. 5B is a cross-sectional view of the infusion set as shown in FIG. 2E along the lines 5B-5B.

Referring now to FIGS. 5A and 5B, the exemplary cap 14 and base 4 are illustrated in an attached and secured position, wherein the tube or opening 16 of the cap 14 aligns with and slidably receives the post 8 of the base 4 to ensure that all the other interacting elements are in alignment as they engage each other. Both the post 8 and tube 16 have generous tapered, contoured, inclined or other similarly functioning lead-in areas 30, 32 to help guide the cap 14 into the correct position on the base 4. FIG. 5B illustrates a side view of FIG. 5A rotated about 90°.

Figure 6A:
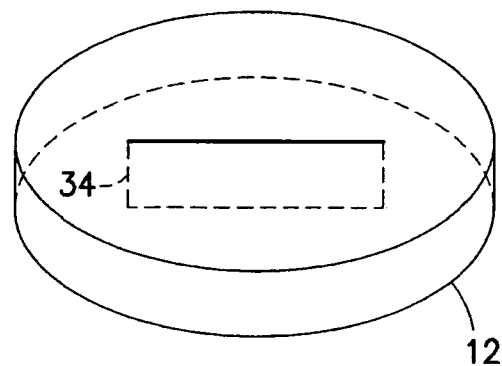
FIG. 6A is a top isometric view of an exemplary slit-septum for use with the infusion set shown in FIG. 2A in accordance with an embodiment of the present invention.
Figure 6B:
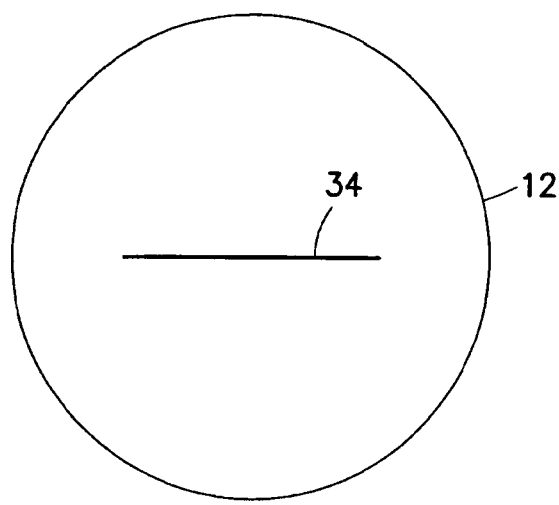
FIGS. 6B and 6C are top views of the slit-septum shown in FIG. 6A before and after needle insertion in accordance with an embodiment of the present invention.

After the tube or opening 16 has aligned with and slidably received the post 8, the blunt cannula 20 penetrates the lower septum 12. The exemplary septa 12 are shown in greater detail in FIGS. 6A-6C. Referring now to FIG. 6A, an exemplary slit 34 extends for a certain distance across the lower septum 12, and from top to bottom of the lower septum 12. The lower septum 12 is designed to be manufactured to be substantially circular and the slit 34 is substantially centered in the lower septum 12. This makes it easier to manufacture the infusion set 100, as no particular orientation of the lower septum 12 is necessary in the base 4. FIG. 6B illustrates the lower septum 12 prior to insertion of the blunt cannula 20. The slit 34 creates a substantially impenetrable seal from top to bottom, or visa-versa, of the lower septum 12. Thus, after the infusion set 100 is installed on the body of the user, and the cap 14 is removed (e.g., for bathing), water, soaps and other foreign materials are substantially prevented from entering the area of the skin where the cannula has pierced the skin. The upper septum 12 can be configured in a substantially identical manner, but is not limited thereto.

Figure 6C:
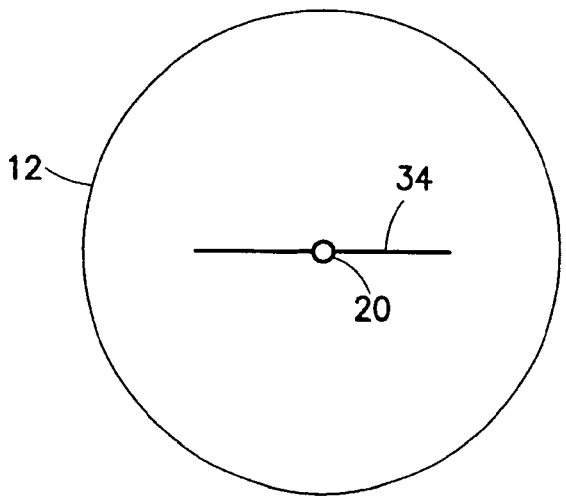

In FIG. 6C, the blunt cannula 20 is shown after it has pierced the lower septum 12 through the slit 34. Because each septum 12 is made of a deformable resilient material, it deforms around the blunt cannula 20, forming a substantially impenetrable seal around the blunt cannula 20. Upon removal of the blunt cannula 20, the slit 34 returns to its original shape as shown in FIG. 6B, again providing the substantially impenetrable seal between the skin and the outside environment. Further, the exemplary septum 12 can be easily sterilized prior to positioning in the device, and can thereafter, be cleaned prior to insertion or re-insertion of the blunt cannula 20 to further reduce the risk of infection. When the blunt cannula 20 penetrates the lower septum 12 during assembly, it allows liquid medication to flow from a luer connector, through the extension tubing 6 and the blunt cannula 20 past the septum 12 and into the catheter 2.

Figure 5C:
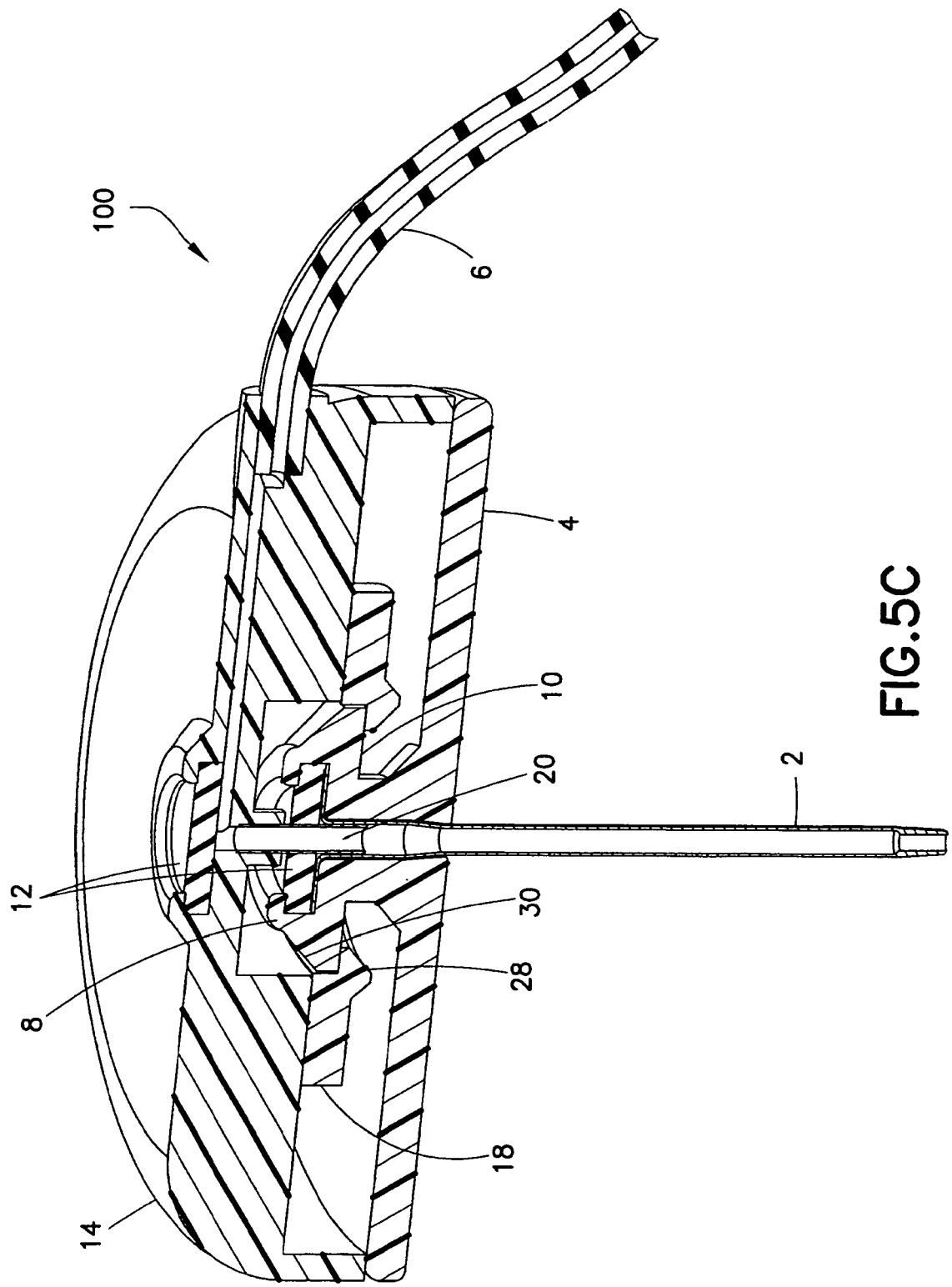
FIG. 5C is an isometric cross-sectional view of the infusion set as shown in FIG. 2E along the lines 5A-5A.

Returning to FIG. 5A, the retention member 18 in the cap 14 is configured to releasably and rotably secure the cap to the base as described in greater detail below, and can be spring loaded, and can be configured to provide tapered, contoured, inclined or other similarly functioning lead-in areas 28 that allow it to contact and be moved out of position by the post 8 lead-ins 30 until clear of the lead-ins 30 at which point it can be configured to springs under the undercut 10 of the post 8 as shown in FIGS. 5A and 5C, thereby locking the cap 14 and base 4 together.

Figure 7A:
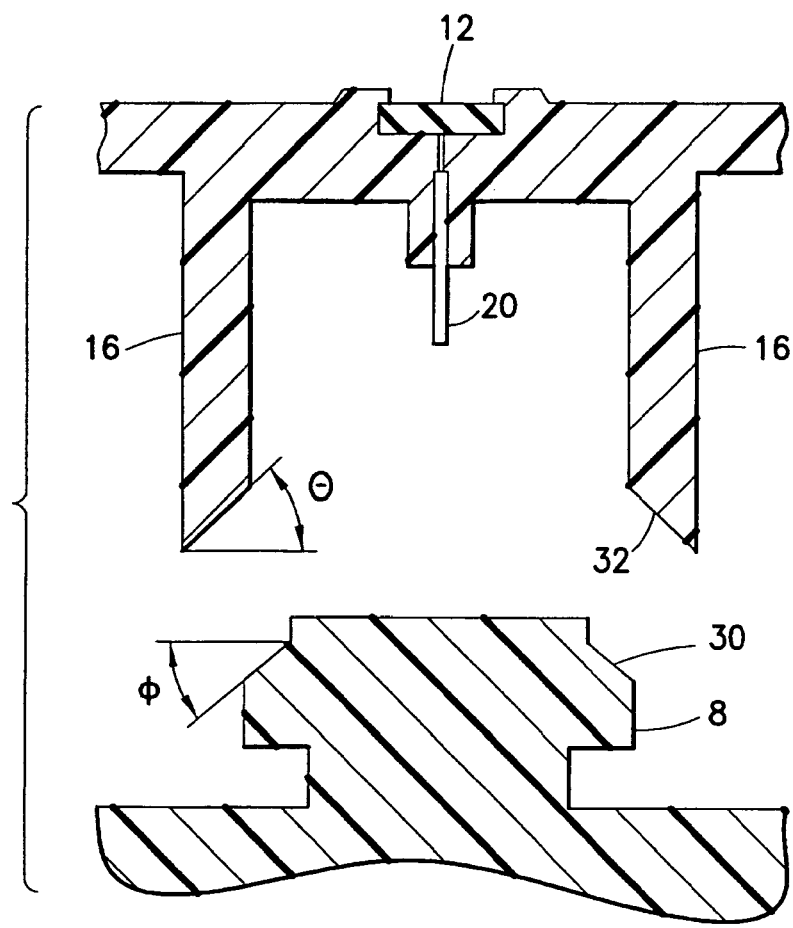
FIG. 7A is an enlarged side view of an exemplary means for aligning the cap and base of the infusion set shown in FIG. 2A in accordance with an embodiment of the present invention.
Figure 7B:
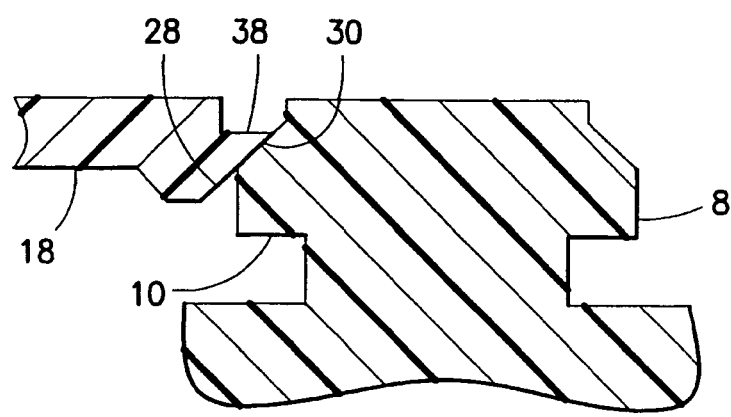
FIG. 7B is an enlarged side view of an exemplary means for retaining the cap to the base of the infusion set shown in FIG. 2A in accordance with an embodiment of the present invention.

FIG. 7A illustrates an enlarged side view of the post 8 and tube or opening 16 with their respective lead-ins 30, 32, and FIG. 7B illustrates an enlarged side view of the post 8 and retention member 18 with their respective lead-ins 30, 28. The angle Θ, formed to create tube lead-in 32, substantially matches the slope and angle Φ of the post lead-in 30, but is not limited thereto. By providing the slope of the post lead-in 30 and the slope of the tube lead-in 32, even if a user misaligns the cap 14 somewhat over the post 8, the respective lead-ins 30, 32 force the two parts (e.g., the cap 14 and the base 4) into alignment. The post 8 can then be slide into the interior space of the tube 16, where the post 8 encounters retention member 18. As such, FIG. 7A illustrates an exemplary means for cap and base alignment with minimal user effort.

As illustrated in FIG. 7B, the retention member 18 lead-in 28 substantially matches in slope the post 8 lead-in 30, but is not limited thereto, so that the user can easily latch the cap 14 onto the base 4. The latching is easily accomplished because the spring-loaded, or otherwise elastically-urged retention member 18 easily moves away from its initial position (i.e., to the left in the example shown in FIG. 7B) as the cap 14 moves down over the post 8. Once the cap 14 has moved down sufficiently such that the blunt cannula 20 has pierced the slit 34 of the lower septum 12, the retention member 18 slides back to the right due to the spring and/or other elastic force, and a detent, shoulder, or other similarly functioning ledge 38 comes in contact with and captures the undercut 10 of the post 8 as shown in FIG. 5A. Of course, the retention means 18 and post 8 also interact in the aforementioned manner when removing the cap 14 from the base 4 at times other then when inserting the cannula 20, or inserting the catheter 2 into the user (i.e., removing the cap 14 for bathing or exercising). As such, FIG. 7B illustrates an exemplary means for rotably and removably securing the cap to the base with minimal user effort.

The latching mechanism of the retention member 18 allows the user to move the retention member 18 against the spring or other elastic urging force, out from under the undercut 10 to thereby allow the cap 14 to be removed from the base 4. The means of releasing the retention member 18 can be integrated in the member 18 itself. Exemplary means of releasing the retention member 18 are described in greater detail below in regard to FIGS. 19-28. The spring force can be created through an actual spring and the retention member 18. In yet other embodiments of the present invention, the retention member 18 can be made integral to the cap 14 and/or the spring force can be generated from the natural bending properties of the materials used to make the cap 14 and a structural design that allows certain parts to flex in response to properly applied forces.

Figure 8A:
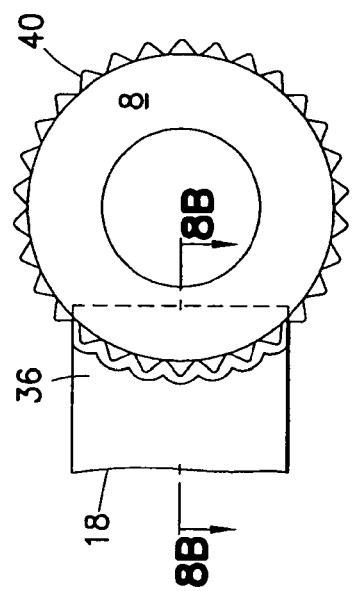
FIG. 8A is an enlarged top view illustrating an operation of an exemplary rotation-locking feature used in the infusion set as shown in FIG. 2A in accordance with an embodiment of the present invention.
Figure 8B:
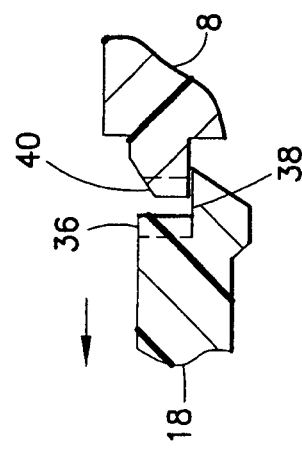
FIG. 8B is an enlarged cross-sectional view of the rotation-locking feature used in the infusion set as shown in FIG. 8A along the lines 8B-8B.

FIGS. 8A and 8B illustrate a first exemplary modification to the infusion set 100 according to the first exemplary embodiment of the present invention. In FIG. 8A, a top view of the post 8 and retention member 18 is shown, wherein the post 8 further comprises one or more post ribs 40 disposed upon an outer circumference, and similarly, the retention member 18 can further comprise one or more retention member ribs 36 upon the and perpendicular to the ledge 38. The post ribs 40 and retention member ribs 36 are substantially similar in profile and arrangement (i.e., configured to engage each other in a mating arrangement), such that they may easily interface with each other and thereby preventing or substantially reducing rotational movement of the cap 14 about the base 4. The user can therefore lock and unlock the cap 14 through the engagement and disengagement of the ribs 36, 40, for rotation of the cap 14 into any desired position, knowing that because of the interlocking post and retention member ribs 40, 36, the cap 14 will not rotate further after engagement, or at least will greatly resist rotation, once adjusted into the desired position. FIG. 8B is an enlarged cross-sectional view along lines 8B-8B of FIG. 8A, and illustrates how the ribs 36, 40 are formed on the retention member 18 and the post 8, and how they interface and align with each other. In the example shown in FIG. 8B, the retention member 18 has been moved to the left and out of engagement by the retention member releasing means (not shown). The cap 18, therefore, is free to be rotated to a new position. However, in such a rotatable position, the retention member 18 has not been disengaged entirely from the base 4, but just from the ribs 40 of the post 8 of the base 4, thus still securing the cap to the base and providing a good seal with the user's skin.

The infusion set 100 according to at least the first exemplary embodiment of the present invention provides substantial advantages over prior art designs. As discussed above, the infusion set 100 does not require much, if any, general alignment between cap and base, and does not require any rotational alignment when connecting the cap to the base. The cap 14 and base 4 easily align with one another, and the cap 14 can rotate freely about the base 4 once the two are attached together, so that the extension tube 6 can be rotated to any desired orientation. As seen in FIGS. 8A and 8B, the post ribs 40 and retention member ribs 36 on the post 8 and retention means 18 allow the user to releasably lock the cap 14 at any desired orientation, or change the orientation after first located while the cap and base remain securely attached to each other. With this configuration, the cap does not rotate freely when the ribs 36, 40 are engaged, but can still be rotated and attached in any orientation when the ribs 36, 40 are disengaged. For example, in an exemplary embodiment of the present invention, the device (or elements thereof) can be aligned and secured, then rotated by the user to a desired position and upon user release of the retention member 18, the device will "lock" into place. The user can push a button or element slightly of the retention member 18, and move the cap out of the locked position temporarily to rotational reposition the cap and then, when released, the device will return to the locked position. In such an exemplary embodiment, the features can be provided to allow alignment, positioning and locking, release and repositioning, and return to locked, all as desired by the user and assisted by elements of the device.

Accordingly, the infusion set 100 according to the first exemplary embodiment of the present invention provides further advantages over the prior art in that it allows the user to connect, with a straight-down motion orthogonal to the body, and without having to manipulate any buttons or levers. Further, the infusion set 100 according to the first exemplary embodiment of the present invention has the advantage of providing the post ribs 40 and retention member ribs 36 that enable the cap 14 and base 4 to automatically be rotationally locked together. This substantially eliminates the chance of dislodging the catheter 2 with any sideways or twisting forces and substantially simplifies the connection process for the user. Accordingly, the cap 14 and base 4 can be easily aligned, assembled and rotated to a desired position using the features of the exemplary post 8, retention member 18, and corresponding retention means lead-ins 28, 30, 32 respectively, as shown and described in FIGS. 7A and 7B. Furthermore, because of the design of the angular lead-ins 28, 30, 32, of the post 8, cap 14, and retention means 18, a user can substantially mis-align the cap 14 and base 4 and yet still easily connect the two, as the two self-align for the final connection. Further, because of the inherent symmetry of the cap 14 and the base 4, a particular orientation is not necessary when aligning the cap 14 and base 4.

Figure 10A:
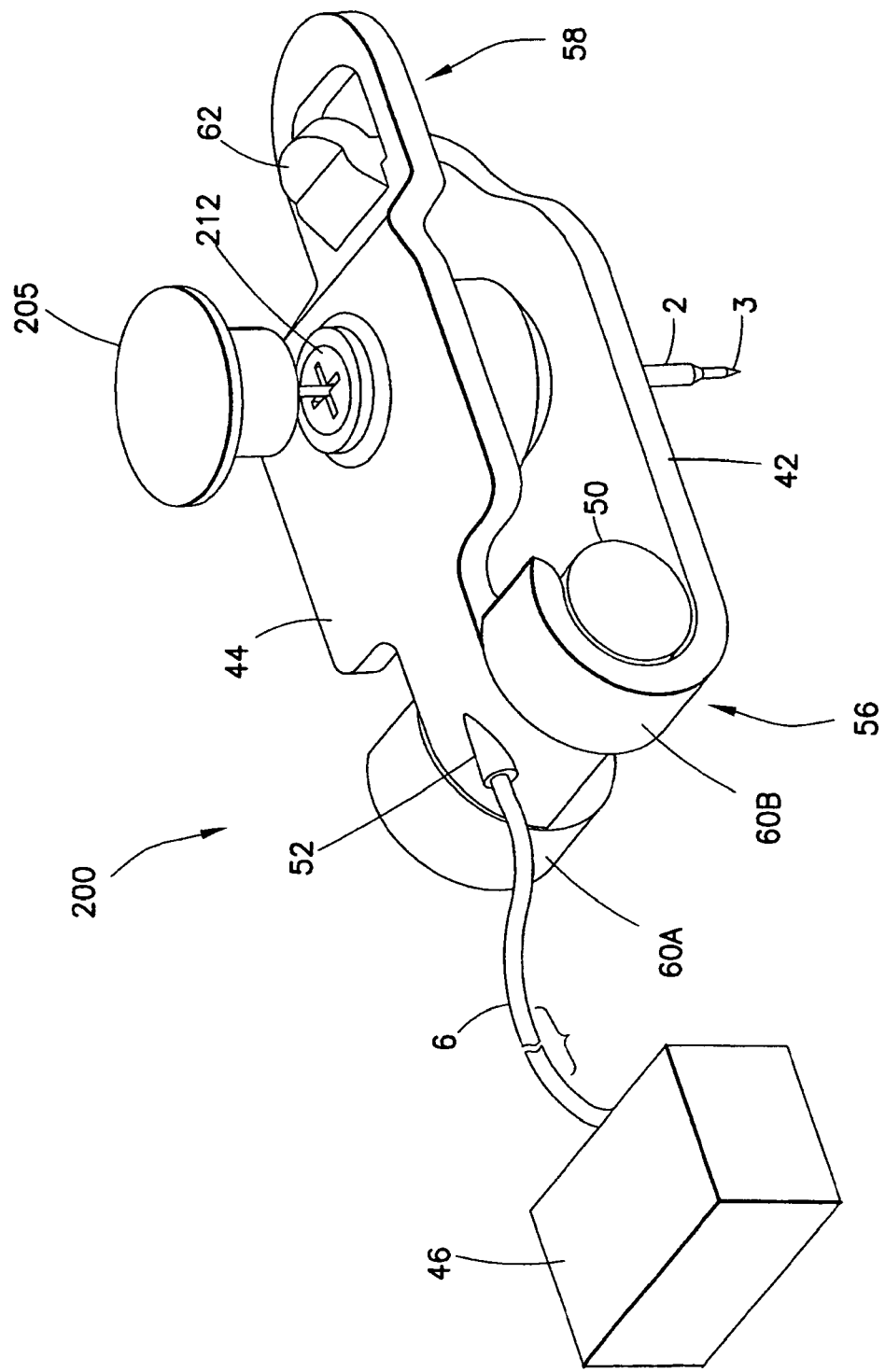
FIG. 10A is a top isometric view of an exemplary infusion set in a pre-insertion state with an alternative needle hub assembly according to a second embodiment of the present invention.

FIG. 10A is a top perspective view of an exemplary infusion set 200 according to a second embodiment of the present invention. The infusion set 200 according to the second embodiment of the present invention comprises a base 42 that includes a catheter 20 and a means of sealing off a fluid path (i.e., septum 212), an introducer blunt cannula 48, and a top fluid cap 44 that is connected to a fluid delivery device, such as a pump 46, via extension tubing 6.

Figure 10B:
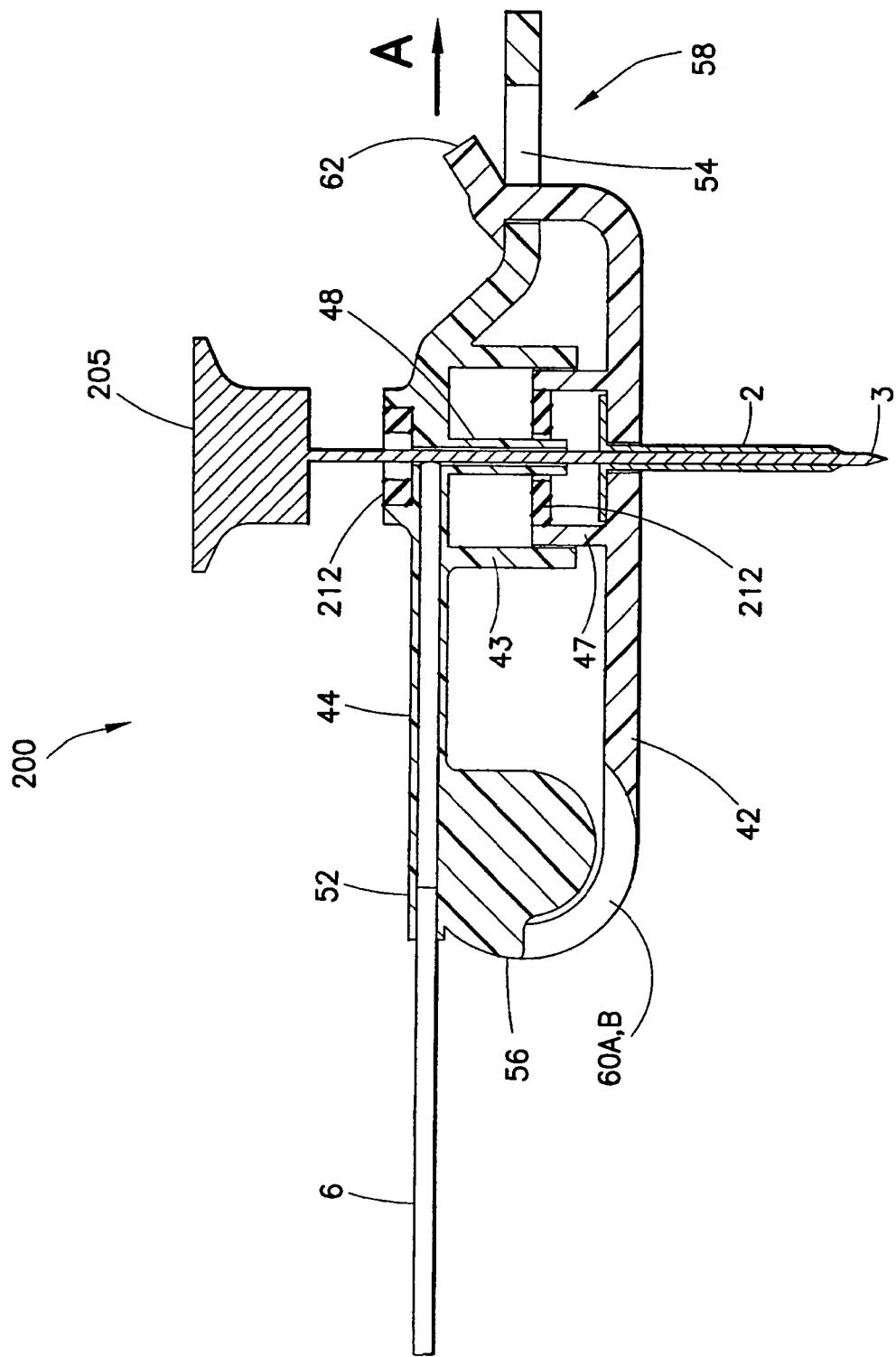
FIG. 10B is a cross-sectional view of the infusion set shown in FIG. 10A.
Figure 12A:
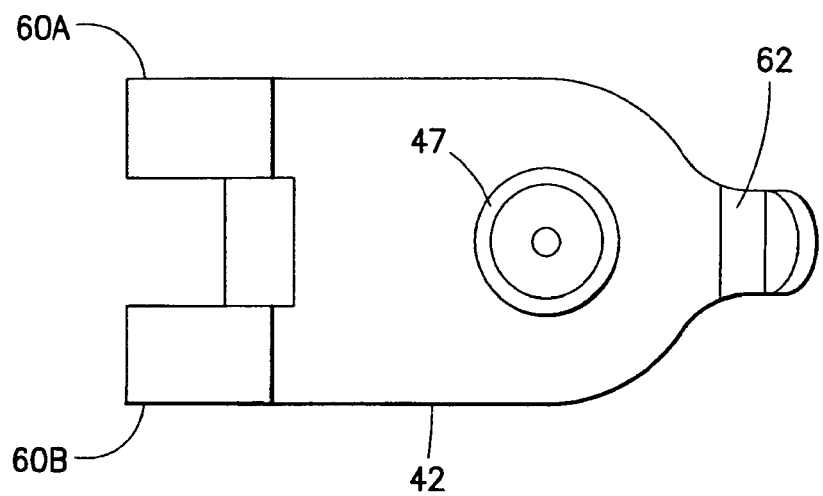
FIGS. 12A and 12B illustrate top and side views of a catheter and connection port assembly for use with the infusion set shown in FIG. 10A in accordance with an embodiment of the present invention.
Figure 12B:
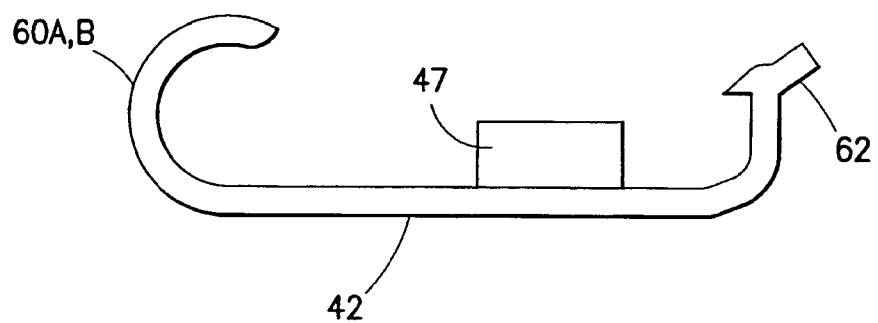

As shown in FIGS. 10A and 10B, there is a rotational interlocking means 56 on, one end of the fluid cap 44 and base portion 42 of the infusion set 200, and a latching interlocking means 58 on the other end of infusion set 200. The rotational interlocking means 56 comprises a cylinder 50 on the fluid cap 44 and a first and second base hook 60A, B on the base 42. FIGS. 12A and 12B illustrate top and side views of the base 42 to illustrate features in greater detail. The first and second base hook 60A, B comprise hooks with a radius that matches the cylinder 50 of the fluid cap 44. That is, the first and second base hook 60A, B comprise hooks with a radius that is configured to rotatably capture the cylinder 50 therein. The materials of the hooks and cylinder therefore, can be selected from any suitable material to provide rotation with minimal wear.

The fluid cap 44 can rotate in a vertical plane relative to the base 42 in an upward direction until the cap 44 no longer obstructs the base 42 and the base 42 is exposed, and can rotate in a downward direction until covering the base 42 and snaps into place by the latching interlocking means 58. In one exemplary embodiment of the present invention, the latching interlocking means 58 can comprise an upwardly projecting and elastically biased latch 62 on the base 42 with one or more detents extending therefrom, and an interlocking hole 54 on the fluid cap 44 for receiving and capturing the upwardly projecting and elastically biased latch 62.

The fluid cap 44 further comprises the blunt cannula 48 that enters the base 42 in an up/down fashion into a septum 212 rather than from the side. The insertion needle 3 is shown inserted through the blunt cannula 48, and a fluid path is created that runs towards the rotatable connection formed by the rotational interlocking means 56. Once the fluid cap 44 is installed, the fluid path is now connected to the blunt cannula 48 and the catheter 20.

To disconnect the infusion set 200 as shown in FIGS. 10A and 10B, the latch 62 is pressed forward relative to the infusion set 200 (i.e., in the direction of the arrow A), allowing the latch 62 to pass through the interlocking hole 54 on the fluid cap 44, thereby releasing it from the base 42. The fluid cap 44 can then rotate out of position and expose the upper surface of the base 42.

Figure 11A:
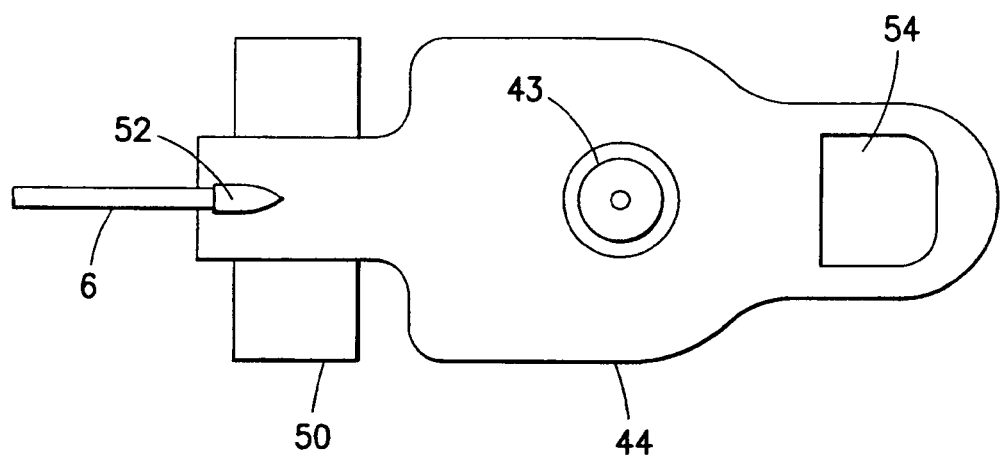
FIGS. 11A and 11B illustrate top and side views of a tubing set connector of the infusion set shown in FIG. 10A in accordance with another exemplary embodiment of the present invention.
Figure 11B:
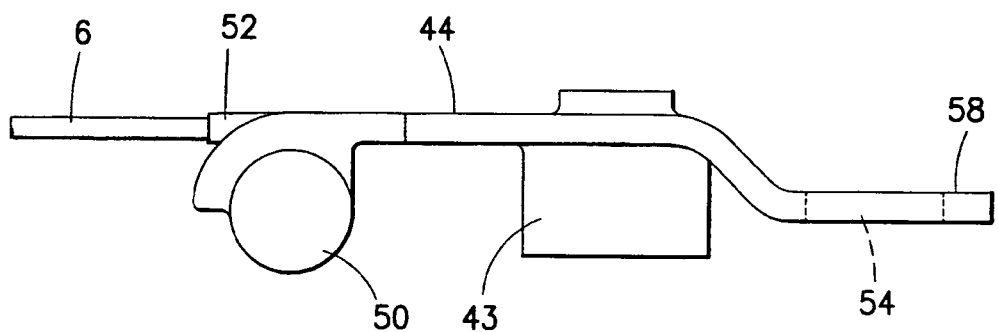
Figure 13:
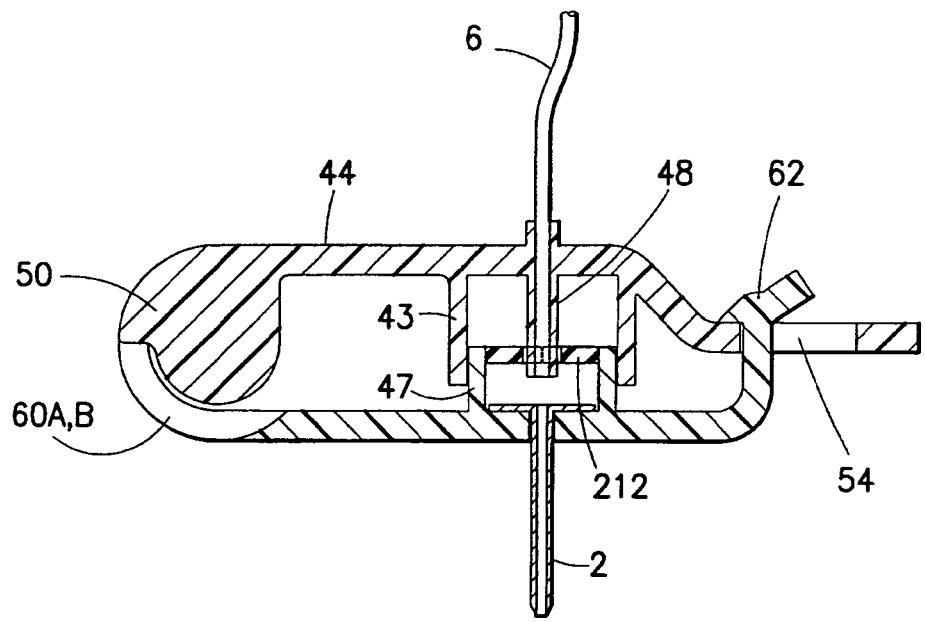
FIG. 13 is a cross-sectional view of the infusion set shown in FIG. 10A with an extension tubing attached to a different location on the tubing set connector than that shown in the infusion set shown in FIG. 10A in accordance with another embodiment of the present invention.

FIGS. 11A and 11B illustrate alternative means for connecting the extension tubing 6 to the infusion set 200 according to the second embodiment of the present invention. In FIGS. 11A and 11B, the extension tubing 6, which can be connected to the pump 46 of FIG. 10A, is connected to a tubing connection 52 that is connected to the cylinder 50 of fluid cap 44. In this exemplary embodiment, the extension tubing 6 forms a "tail" from the infusion set 200, in a horizontal manner. In yet other exemplary embodiments of the present invention, the extension tubing 6 can be connected to a tubing connection that is located on the center top portion of the fluid cap 44 as shown in FIG. 13. In this case, the extension tubing 6 extends nearly vertically from the fluid cap 44. A user can be provided with both fluid caps 44, thereby providing the user with increased flexibility in administering the medicine to themselves, and in controlling the infusion set profile one in position.

Figure 14:
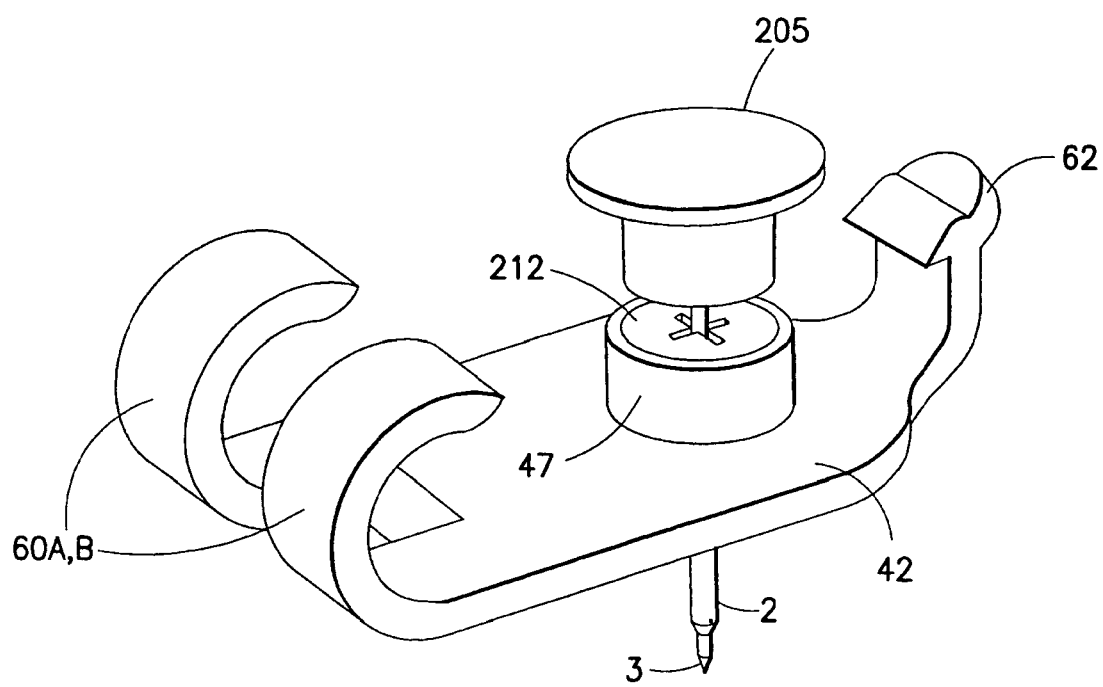
FIG. 14 is a top isometric view of the needle hub assembly being inserted into the catheter and connection port assembly of the infusion set shown in FIG. 10A in accordance with an embodiment of the present invention.

As shown in FIGS. 10A, 10B and 14, the fluid cap 44 can comprise a top septum 212 on an upper surface, and an opening 43 extending from a lower surface and surrounding the blunt cannula 48. The base 42 can be provided with a lower septum 212 on an upper surface, and which is surrounded by a projection 47. When the top 44 is rotably assembled with the base 42, the projection 47 aligns with and is slidably received by the opening 43. Further, the blunt cannula 48 of the cap 44 is introduced through the lower septum 212 from the top of the lower septum 212, which adds advantages over certain prior art infusion sets, especially in regard to contamination. The infusion set 200 according to the second exemplary embodiment of the present invention substantially eliminates the possibility of contamination and infection. The rotational interlocking means 56 provides an easy means for connecting the fluid cap 44 to the base 42, and the latching interlocking means 58 provides an easy method for securing both the fluid cap 44 to, and releasing the fluid cap 44 from, the base 42.

FIGS. 10A, 10B and 14 illustrate two methods for inserting the catheter 2 into a patient. In FIGS. 10A and 10B, the needle 3 is inserted through the upper septum 212 located in the fluid cap 44. The needle 3 passes through the upper septum 212 in the blunt cannula 48 which passes through the lower septum 212, and finally into the catheter 2. The needle grip 205 aids the patient in inserting the needle 3, and once the needle 3 is inserted through the blunt cannula 48 and catheter 2, the user can then insert the catheter into their body for use to administer liquid medication.

FIG. 14 illustrates an alternative method for inserting the catheter 2 into the patient's body. In FIG. 14, the cap 44 is not shown but illustrates the exposed upper surface of the base 42 that would be provided by rotating the cap 44 away from the base. In FIG. 14, the user does not insert the needle 3 through the upper septum 212 in the fluid cap 44. Instead, the user simply inserts the needle 3 directly through the lower septum 212 in the base 42 and through the catheter 2. The catheter 2 can then be inserted into the patient's body, and the base 42 attached to skin.

The first and second exemplary embodiments of the present invention (e.g., infusion sets 100, 200) can be modified for still further improved performance as desired, such as, for example, to allow a patient to prime the infusion sets 100, 200. Priming is the process whereby liquid medication is pumped into the infusion sets 100, 200 before the catheter 2 is inserted into the patient's body. The purpose of this is to ensure that the pump 46 delivers the proper amount of medication to the patient over a given period of time. If the catheter 2 is inserted dry, i.e. with no liquid medication already present, there is a lag between the time the pump 46 is started and the time the medication enters the body. If the patient merely tracks the time the pump is on, he or she may be significantly under-medicated.

Figure 9:
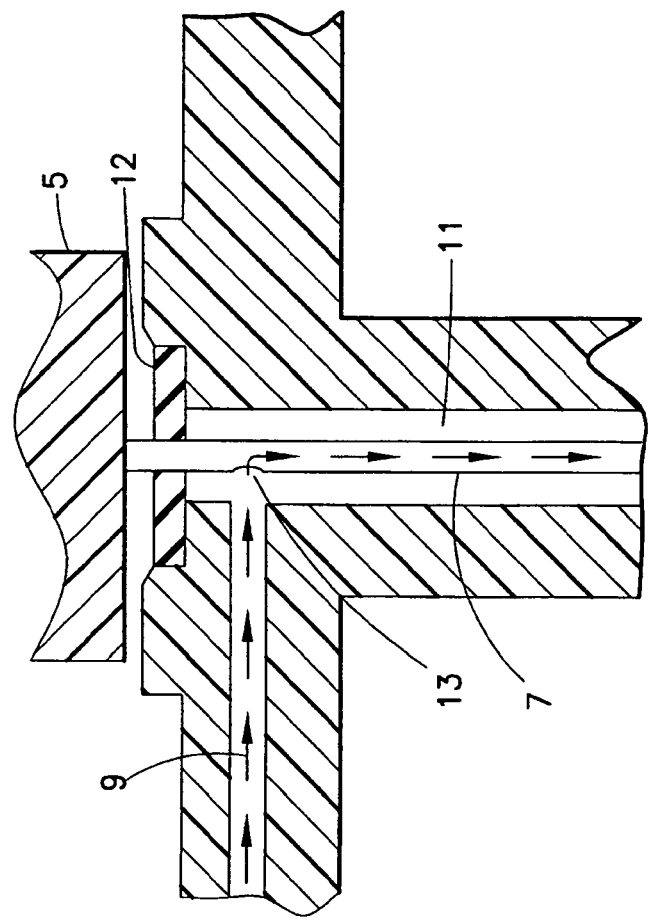
FIG. 9 is an enlarged cross-sectional view of an alternative needle hub assembly following insertion into the infusion set for use with the infusion set as shown in FIG. 2A in accordance with an embodiment of the present invention.

To prime the infusion set, an exemplary modified needle 7 can be used as illustrated in FIG. 9. The modified needle 7 is hollow and comprises one or more holes 13 at a location where, once it is inserted through the blunt cannula 20, the medication 9 can enter the needle 7 through the hole 13 and flow through it. In the infusion set shown in FIGS. 7 and 8, the exemplary hole 13 in the modified needle 7 would be at a point on the modified needle 7 that is just below the upper septum 12. This is fairly close to the needle grip 5 as illustrated in FIG. 9. The modified needle 7 is hollow and comprises the exemplary hole 13 at the top close to the needle grip 5. The medication 9, exhibited as the arrows of FIG. 9, flows into the infusion set and into the needle passageway 11. The medication 9 also flows into the hollow modified needle 7 through the hole 13, eventually filling the modified needle 7 until it exits at its end (located at the bottom of the blunt cannula 20). The infusion set is now primed, and the patient can more accurately measure the amount of medication administered into the patient's body.

Figure 15:
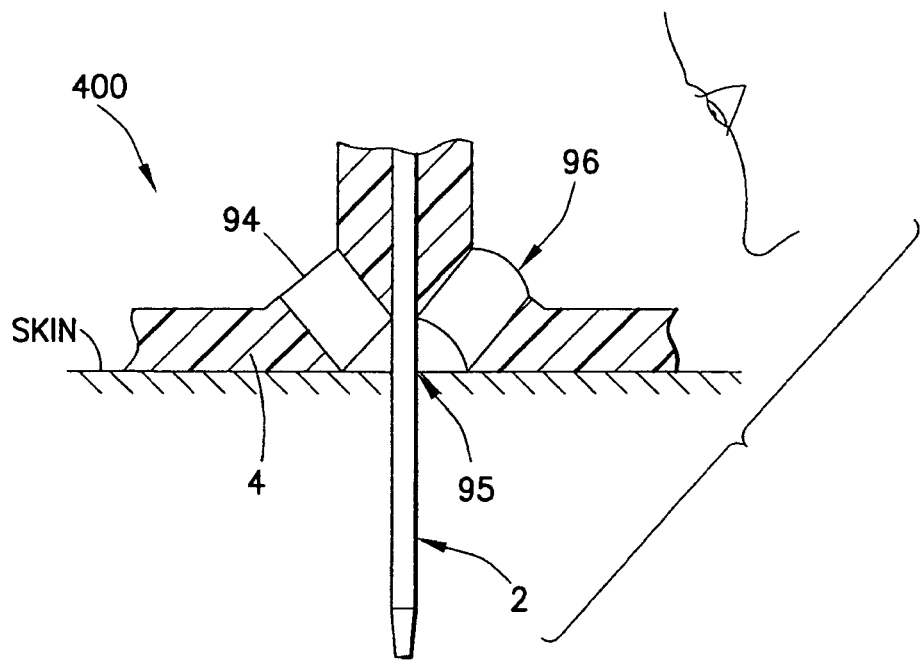
FIG. 15 is an enlarged cross-sectional view of an exemplary lens arrangement for use with an exemplary infusion set for viewing a catheter-skin insertion site of the infusion set according to a third embodiment of the present invention.

FIG. 15 is an enlarged cross-sectional view of an exemplary lens arrangement for viewing a catheter-skin insertion site of an infusion set according to a third embodiment of the present invention. The exemplary window arrangement of FIG. 15 illustrates the third embodiment of the present invention that can be added to any one of the infusion sets disclosed herein, or any other suitable infusion set as desired. The exemplary infusion set 400 used to illustrate the lens arrangement can comprise any of the base components 4, 42, of the infusion sets 100, 200, combined with the additional features of any combination of an opening, into which a clear flat lens 94 and/or a clear magnified lens 96 can be secured. In the following description, for purposes of conciseness only and not in a limiting sense, the description shall be made in reference to the first embodiment of the infusion set 100 only.

The base 4 of the infusion set 100 can include either one or two lenses 94, 96 for the user to be able to see the insertion site 95 where the catheter 2 enters the skin. The lenses 94, 96 are, in a preferred embodiment, made of transparent plastic. One skilled in the art can appreciate, however, that other suitable materials can also be used. In yet another exemplary embodiment of the present invention, no lens are provided and instead, an opening can be provided in the base 4 through which the user can see the insertion site 95 where the catheter 2 enters the skin. The clear plastic lenses 94, 96 can be designed and molded such that a user can see clearly through them. The base 4 can be sealed entirely around the insertion site 95 with adhesive tape, or any other adhesive means, as described above. This helps to maintain sterility of the insertion site 95 while allowing the user to view it for signs of irritation or infection. The clear flat lens 94 typically provides little or no magnification. The clear magnified lens 96 is typically curved on either the top, bottom or both surfaces to provide some magnification to assist the user in discerning that the insertion site is either free or not free of infection or irritation.

The use of the clear plastic lenses 94, 96 in any of the above-described embodiments 100, 200, or other infusion sets not discussed herein, provides the user with the opportunity to keep the insertion site 95 cleaner and more sterile. Furthermore, the third exemplary embodiment of the present invention allows the user to detect the first signs of infection at the insertion site, improper insertion or extraction of the catheter 2, or any other irregularity at the insertion site. This is an advantage over the prior art designs that do not provide any means, other than the removal of the base, to monitor the insertion site for infections.

Figure 16:
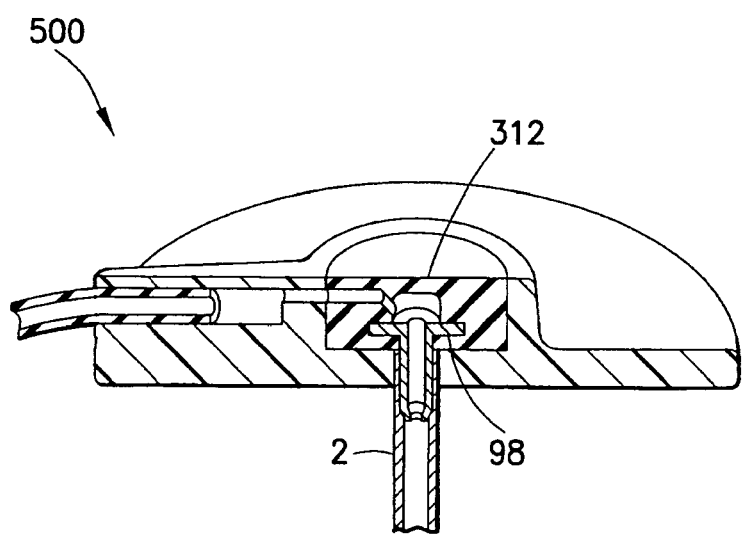
FIG. 16 is an isometric cross-sectional view of an exemplary septum holding arrangement according to a fourth embodiment of the present invention.
Figure 17:
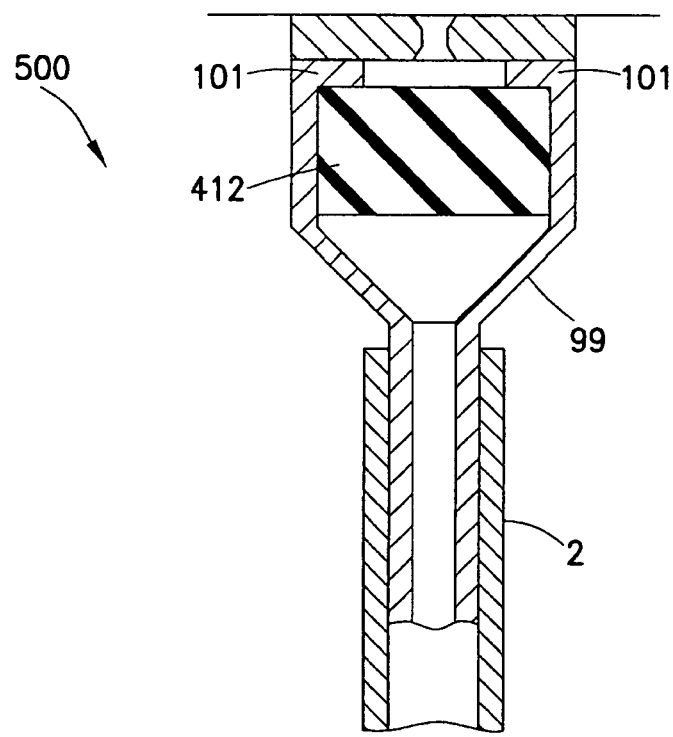
FIG. 17 is an enlarged cross-sectional view of another exemplary septum holding device according to the fourth embodiment of the present invention.
Figure 18:
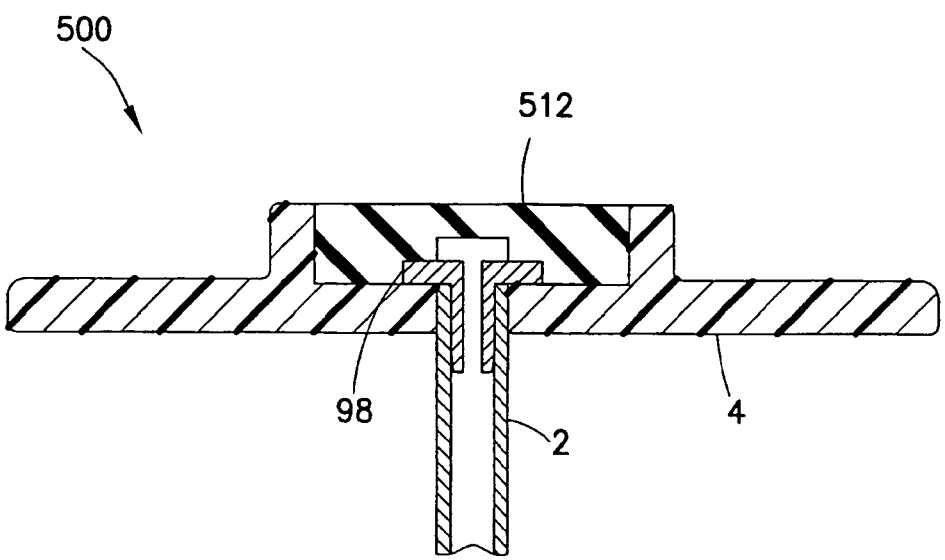
FIG. 18 is an enlarged cross-sectional view of still another exemplary septum holding device according to the fourth embodiment of the present invention.

FIGS. 16 through 18 illustrate several exemplary septum holding sets according to the fourth embodiment of the present invention that can be added to any or all of the infusion sets disclosed herein, as well as other suitable infusion sets. FIG. 16 illustrates a first example of an exemplary wedge-in-a-septum arrangement according to the fourth embodiment of the present invention. As can be seen in FIG. 16, the wedge 98 is encapsulated by the septum 312 of the infusion set 500. The wedge 98 provides one or more shoulders, detent or other features which are captured within a corresponding opening in an inner portion of the septum 312. The wedge 98 further comprises a perpendicular member extending downward and slightly beyond the septum 312. In doing so, one function of the wedge 98 is to fix in place and locate the catheter 2. The septum 312 of FIG. 16 is then fixed in place and remains in place, regardless of repeated insertions by the needle 3 (not currently shown). In an exemplary embodiment, the wedge 98 can be constructed of metal, plastic or other suitable material or combination of materials.

The exemplary septum-wedge arrangement of FIG. 17 comprises the catheter 2 over a septum-enclosing wedge 99 with the septum 412 that is housed inside the septum-enclosing wedge 99. As shown in FIG. 17, the exemplary septum-enclosing wedge 99 comprises an enlarged upper portion to receive, enclose and capture the septum 412, and a narrow lower portion to fit within the catheter 2. In doing so, the septum-enclosing wedge 99 is designed such that a top edge 101 of the septum-enclosing wedge 99 can be forced over the septum 412 to prevent dislodgment of the septum from the base assemblies 4, 42, of the infusion sets 100, 200.

Another exemplary septum-wedge arrangement is shown in FIG. 18. In FIG. 16, the septum-fixing wedge 98 is fixed inside the septum 312. In FIG. 18, the septum-fixing wedge 98 is fixed below the septum 512, which can comprise a recess for receiving the shoulder of the septum-fixing wedge 98, and resides on top of the catheter 2 and/or base 4. The exemplary septum holding arrangement shown in FIG. 18 is a second example of the wedge-in-a-septum arrangement as shown in FIG. 16. In FIG. 18, the septum 512 also encapsulates wedge 98, but not as completely (as described above) as in FIG. 16.

In the first, second and third exemplary septum-wedge arrangements according to the fourth embodiment of the present invention, the septum 312, 412, 512, is not free to become dislodged, and remains substantially fixed in location even after numerous insertions of the needle 3. An advantage of the first, second and third exemplary septum-wedge arrangements according to the fourth embodiment of the present invention is that a secondary part is not necessary to hold the septum in place during manufacturing, therefore reducing part inventory and manufacturing costs.

Figure 19A:
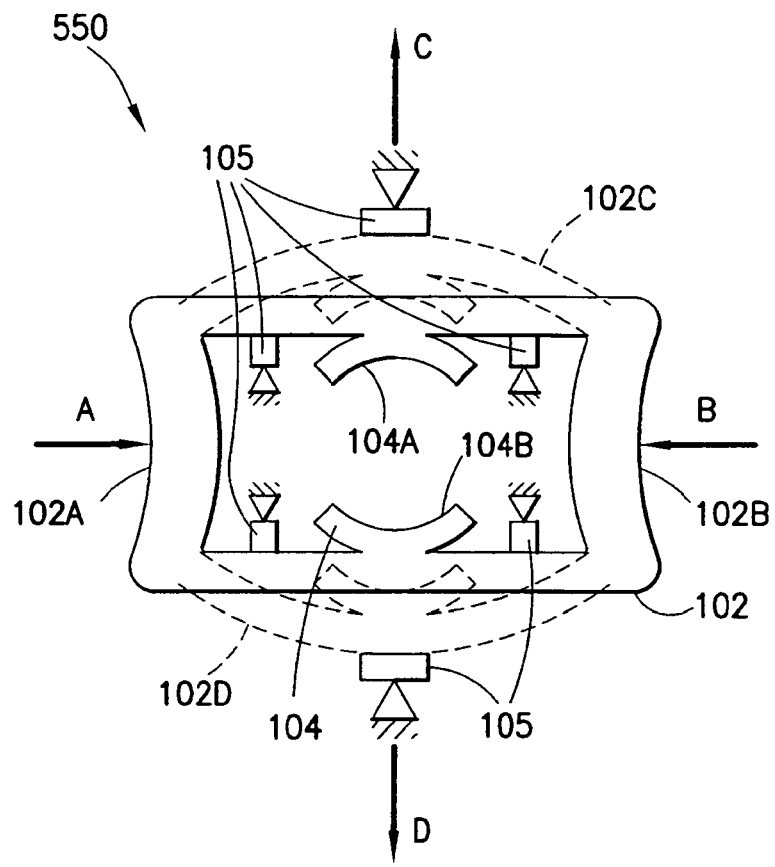
FIGS. 19A and 19B are bottom and top views of an exemplary latching mechanism to connect a tubing set to a connection port assembly of an exemplary infusion set according to a fifth embodiment of the present invention.
Figure 19B:
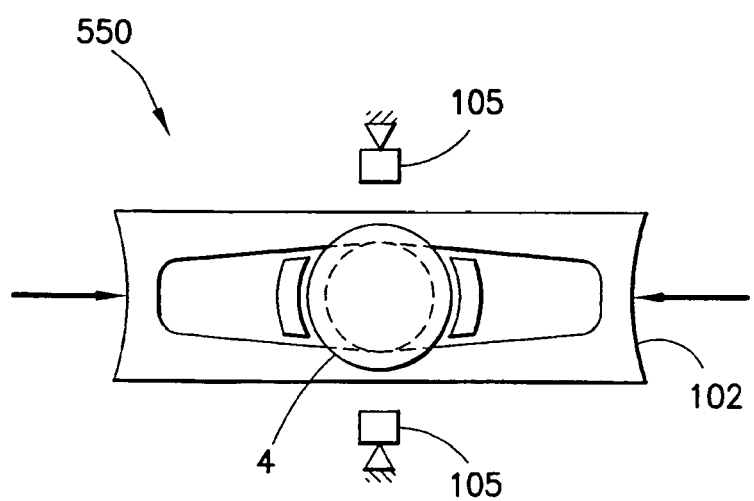

FIGS. 19A and 19B illustrate bottom and top views of an exemplary cap retention means 550 according to a fifth embodiment of the present invention. The fifth embodiment of the present invention comprises a flexible cap element 102 that can be provided within cap 14 or in place of cap 14, and which is secured to the base 4 by a retention means 104. The flexible cap element 102, as shown in FIGS. 19A and 19B, can be referred to as a dual-sided, flexible-hoop cap element 102 comprising sides 102A, 102B, 102C, 102D, and can be used with the infusion set 100 according to at least the first embodiment of the present invention that includes the base 4, and all of its attendant features. As described above, the elements to which an exemplary cap is secured is comprised of the base 4 which has the post 8 with the undercut 10, catheter 2 and septum 12 to seal the proximal end of the catheter 2. A connection set (i.e., such as the flexible-hoop cap element 102) comprises the tube or opening 16, a retention member, a means for releasing the retention member, the blunt cannula and blunt cannula cover 20, and the extension tubing 6 with a luer connector (not currently shown).

Referring to FIGS. 19A and 19B, an exemplary operation of the cap retention means 550 according to the fifth embodiment of the present invention will now be described. Note that the above-described features and details in regard to the cap 14 and base 4 (e.g., blunt cannula, septa, and so forth) are still present but have been omitted from the drawings in order to illustrate more concisely operation of the infusion set according to the fifth through eleventh embodiments of the present invention described in greater detail below.

The flexible-hoop cap element 102 works in accordance with the principle that if opposite sides of a flexible-hoop are compressed, the two sides that are about 90 degrees (i.e., perpendicular) relative to the sides upon which the compression force is applied, will be moved apart by the compression force. In this example, the flexible-hoop cap element 102 will have an exemplary compression force applied to sides 102A, B and in doing so, sides 102C, D will be forced apart. The retention member 104 comprises at least the projections 104A, 104B, disposed on an inner surface of the sides 102C, D of the flexible-hoop cap element 102. The projections can comprise any suitable shape, including the partial, contour shape of FIG. 19A, that can be used to capture and release the post 8 through the deflection of the sides 102C, D. In yet other embodiments, only one projection can be provided to capture the post 8. Further, one or more elements of the set can comprise elements 105 to serve as guides for alignment and travel limits during the operation of the flexible-hoop cap element 102.

An exemplary flexible-hoop cap element 102 can be circular, square, rectangular, hexagonal or any other polygonal shape. In one exemplary embodiment, the flexible-hoop is in the shape of a rectangle or hexagon. For purposes of this discussion, a rectangular shape will be used as an example. However, this example is not meant to be limiting, as any polygonal shape can be used, as discussed above.

In an exemplary operation of the flexible-hoop cap element 102, the post 8 (not currently shown) is positioned in the center of the flexible-hoop cap element 102. The retention member 104A, B interfaces with the undercut 10 on the post 8, since each is attached to approximately the center of each of sides 102C, D. As the user applies an inward force on the short sides 102A, B of the flexible-hoop cap element 102 along the force arrows A, B, the long sides 102C, D bow outward in the direction of force arrows C, D, moving the retention member 104A, B away from the post 8 and releasing the undercut 10.

Various modifications and alterations can be made to the flexible-hoop cap element 102. For example, the long sides 102C, D can be biased to bend in the desired direction. Further, the flexible-hoop cap element 102 can be weakened at the corners and/or center of the long sides 102C, D to help and control the bending. The flexible-hoop cap element 102 can also be made of one or multiple pieces. If the flexible-hoop cap element 102 is made of multiple pieces, flexibility can be imparted into in one or more of the separate pieces, hinges can be used where the pieces join, and/or a flexible joining material (e.g., an adhesive) can be used. The natural spring action of the material can also be used to keep the retention members 104A, B engaged with the post 8 when not activated, or additional springs can be added to facilitate the natural retaining force of the flexible-hoop cap element 102. For example, a spring or springs can be provided to stretch across the flexible-hoop cap element 102 from the first long side 102C to the second long side 102D. Further, both short sides 102A, B of the flexible-hoop cap element 102 can move, or one side can be fixed to the cap 14, with only one side permitted to move. Still further, the flexible-hoop cap element 102 does not have to form a complete hoop, but can be one-sided such that features of only one side (i.e., 104A) can be used to secure the cap.

Figure 20A:
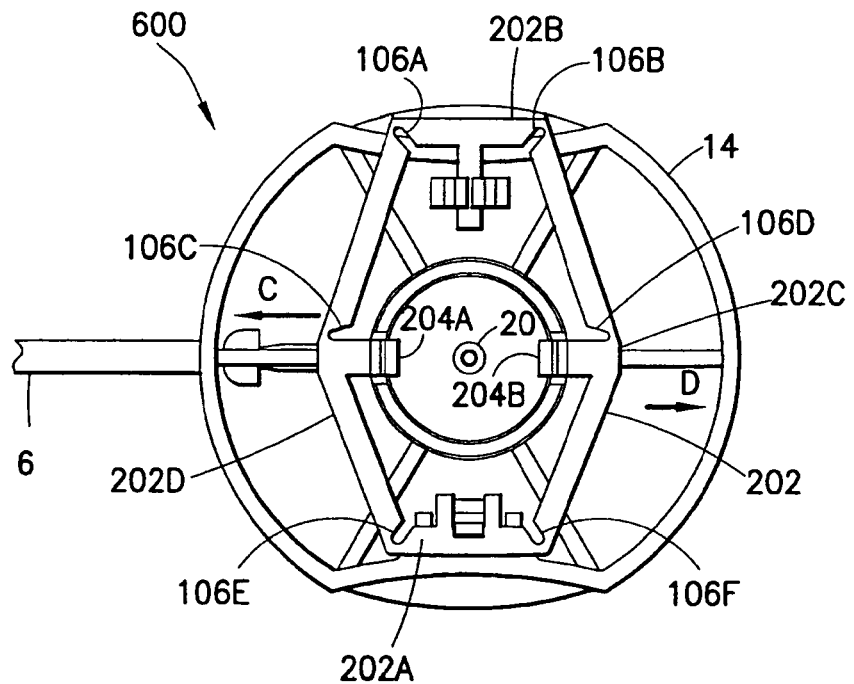
FIGS. 20A and 20B are bottom views of an exemplary modification to the latching mechanism to connect a tubing set to a connection port assembly shown in FIGS. 19A and 19B in accordance with an embodiment of the present invention.
Figure 20B:
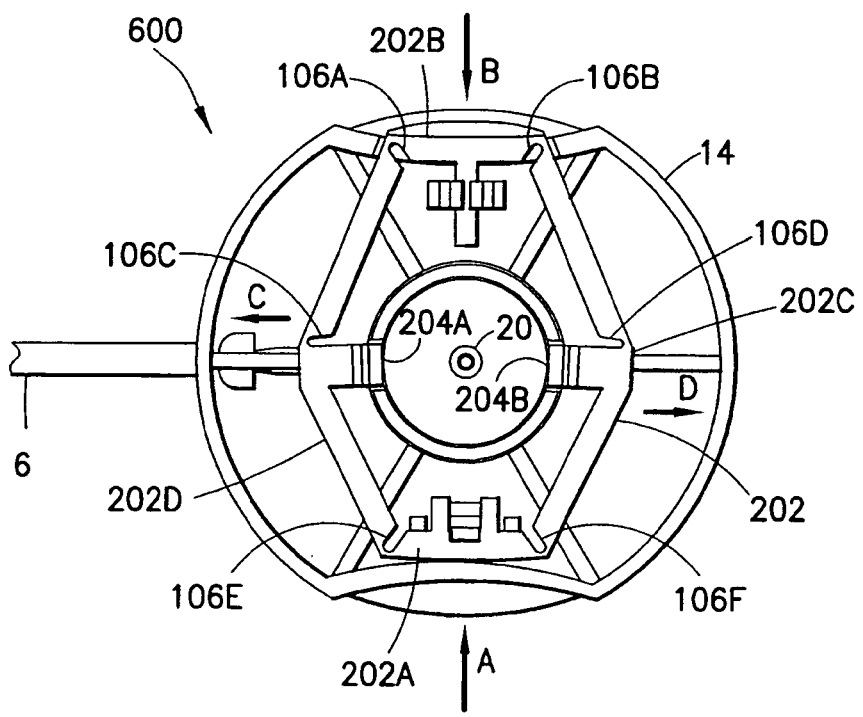

FIGS. 20A and 20B, as discussed above briefly in regard to FIGS. 3A-3E, illustrate a modification of the cap retention means 550 according to the fifth embodiment of the present invention shown in FIGS. 19A and 19B. FIGS. 20A and 20B illustrate a bottom view of another exemplary cap retention means 600 that can be provided within cap 14 or in place of cap 14. In FIG. 20A, the flexible-hoop cap element 202, shown within the cap 14, is in a relaxed state. This is the state of the cap retention means 600 prior to, or after attachment to the base 4. In FIG. 20B, mutually applied forces, represented by arrows A, B, are applied to the flexible-hoop cap element 202 at sides 202A, B. According to the above-discussed principles of bending, the long sides 202C, D of the flexible-hoop cap element 202 bend outward in the direction of arrows C, D due to the applied forces. Note that in this embodiment of the present invention of the flexible-hoop cap element 202, the sides 202C, D are biased outwardly.

Figure 21A:
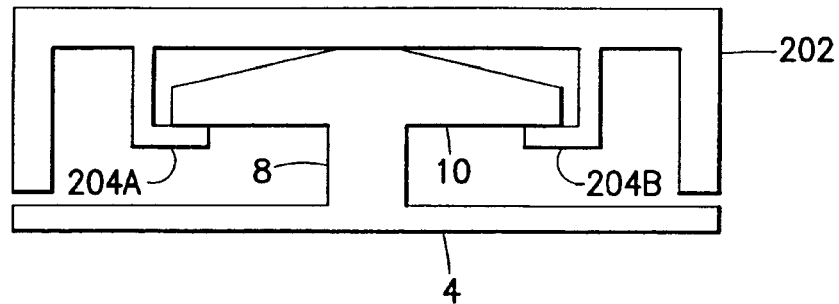
FIGS. 21A and 21B are cross-sectional views of an exemplary modification to the latching mechanism to connect a tubing set to a connection port assembly shown in FIGS. 20A and 20B illustrating the interaction between first and second hoop cap retention members and a post of the connection port assembly in accordance with another embodiment of the present invention.
Figure 21B:
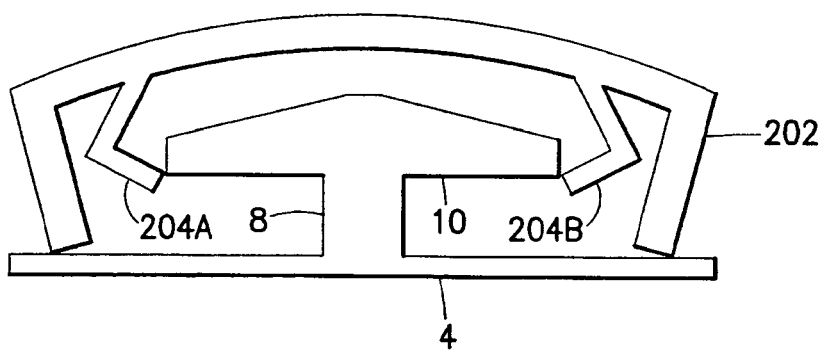

The first and second flexible-hoop cap retention member 204A, B also moves outward with sides 202C, D. FIGS. 21A and 21B illustrate simplified side views of the flexible hoop cap element 202 fitted over the base 4 of FIGS. 20A and 20B. The first and second hoop-cap retention members 204A, B fit under the undercut 10 on the post 8, thereby locking the flexible-hoop cap element 202 onto the base 4. FIG. 21B illustrates the relationship between the first and second flexible-hoop cap retention member 204A, B and the undercut 10 on the post 8 when the sides 202A, B (see FIGS. 20A and 20B) of the flexible-hoop cap element 202 have been pushed inwardly in the direction of arrows A, B (see FIGS. 20A and 20B). Because of the omni-directional configuration of the first and second flexible-hoop cap retention member 204A, B and the post 8, the flexible-hoop cap element 202 can be locked onto the base 4 in almost any direction. In yet another embodiment of the present invention illustrated in FIG. 21B, a modification to the embodiment of FIGS. 20A, B and 21A can be provided, wherein the top of element 202 can be pressed downward in the center, thus causing the elements 204A, B to be pushed outward. In doing so, the contour of the disengagement shown in FIG. 21B would be substantially reversed, but still result in the release of the undercut 10 of the post 8.

The flexible-hoop cap element 102, 202 can also be fabricated with several cut-away, or weakened portions, to facilitate bending of the sides. In FIGS. 20A, B, such exemplary portions are shown as weakened portions 106A-F, and can be provided and located to facilitate movement of the sides 102A-D, 202A-D, in the desired directions. A user therefore is required to apply a lesser force according to arrows A, B when putting the cap retention means 550, 600 onto the base 4, or removing the cap retention means 550, 600 from the base 4.

Figure 22:
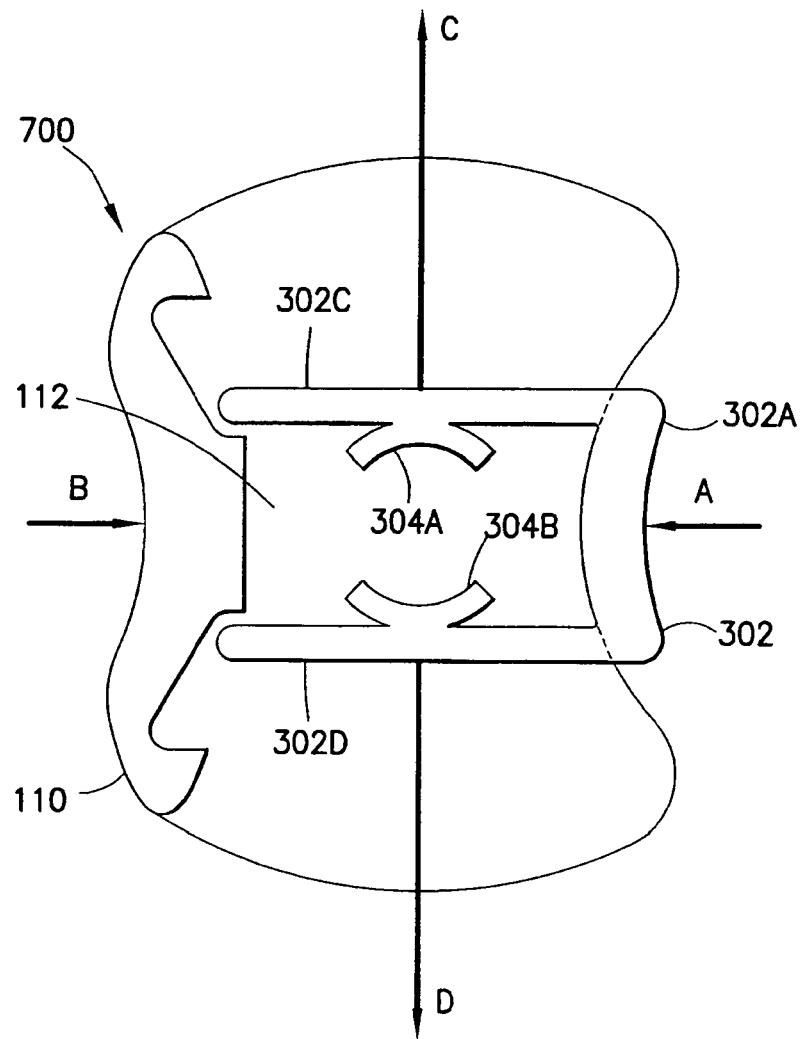
FIG. 22 is a top view of an exemplary latching mechanism to connect a tubing set to a connection port assembly of an exemplary infusion set according to a sixth embodiment of the present invention.

FIG. 22 illustrates a top view of another exemplary cap retention means 700 according to a sixth embodiment of the present invention. The cap retention means according to the sixth embodiment of the present invention comprises an open-ended "U-shaped" flexible-hoop cap element 302 and an extending wedge 110 that can be provided within cap 14 or in place of cap 14. As shown in FIG. 22, the U-shaped flexible-hoop cap element 302 comprises the sides 302A, C, D, and the retention members 304A, B, attached to inner surfaces substantially as described above. The remaining side of the cap element 302 is left open.

In operation, the sides 302C, D are flexed apart in the direction of arrows C, D, by the application of a user applied force in the direction of arrow A, which introduces the extending wedge 110 into the open end 112 of the U-shaped flexible-hoop cap element 302 in the direction of arrow B. Such movement of the cap element 302 results in the sides 302C, D being displaced outwardly by the incline of the wedge 110, thereby releasing the post 8 (not currently shown) from the retention members 304A, B.

As with the other cap retention means discussed above, various modifications and alterations can be made to the cap retention means 700. For example, the U-shaped flexible-hoop cap element 302 can be fixed to the cap 14 such that the extending wedge 110 is movable between a securing and releasing position, or the extending wedge 110 can be fixed to the cap 14 such that the U-shaped flexible-hoop cap element 302 is movable between a securing and releasing position. In still another exemplary embodiment of the present invention, both the extending wedge 110 and the U-shaped flexible-hoop cap element 302 can be made movable. Further, the extending wedge 110 can comprise one or more ramped slots (not shown) in the cap 14, with posts on the U-shaped flexible-hoop cap for guidance through engagement with the slots, or using a similar but reversed arraignment.

The U-shaped flexible-hoop cap element 302 can be made of one piece or multiple pieces joined together. The extending wedge 110 can be made part of the U-shaped flexible hoop cap element 302 with a living hinge (not shown) to allow the extending wedge 110 to move. The U-shaped flexible-hoop cap element 302 can also have weakened areas to allow the deflection (as shown in the embodiment of the flexible-hoop cap element 202), and/or can have hinges to provide other desired flexibility. The extending wedge 110, in relation to the U-shaped flexible-hoop cap element 302 and the sides 302A, C, D, of the U-shaped flexible-hoop cap element 302 can be self-sprung or can have external springs. In an exemplary operation, the extending wedge 110 is pressed into the opening 112, and with the application of force applied in the directions indicated by arrows A and B, the sides 302C, D, are forced open in the direction of arrows C, D.

Figure 23A:
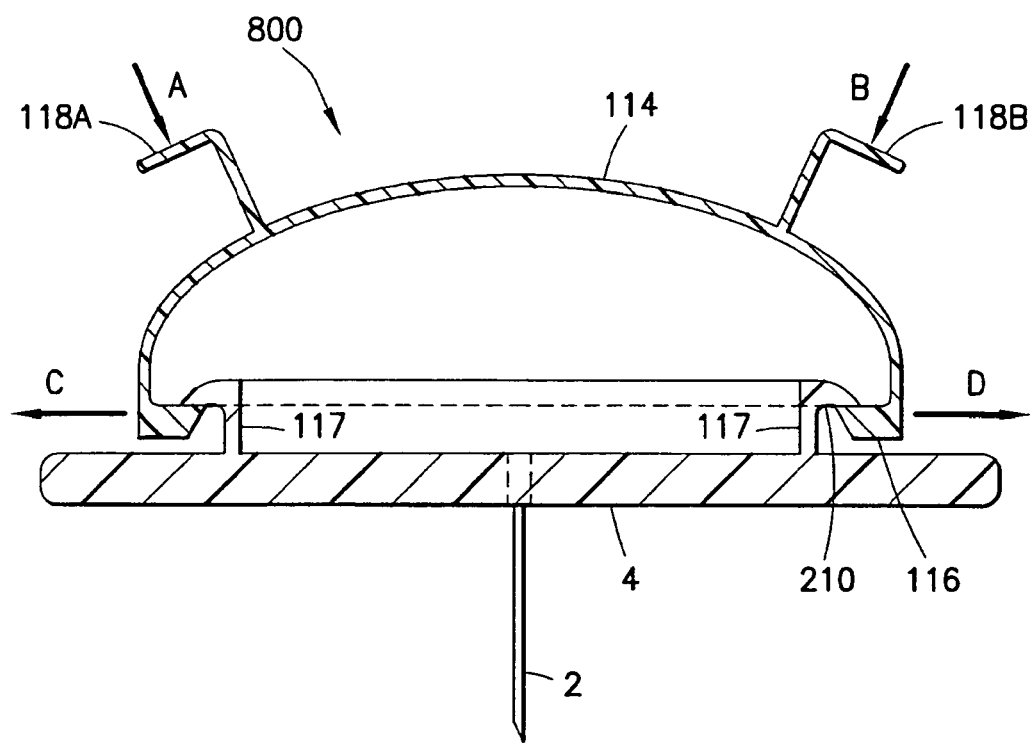
FIGS. 23A and 23B are enlarged cross-sectional views of an exemplary latching mechanism to connect a tubing set to a connection port assembly of an exemplary infusion set according to a seventh embodiment of the present invention.
Figure 23B:
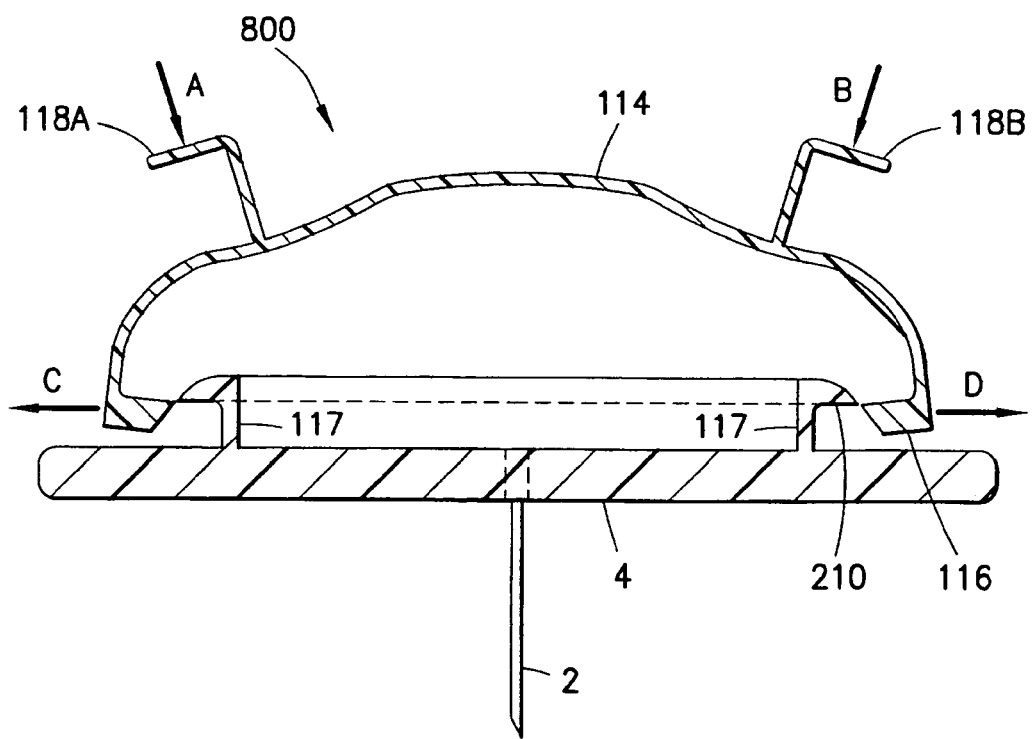

FIGS. 23A and 23B illustrate side views of another exemplary cap retention means 800 according to a seventh embodiment of the present invention. As shown in FIG. 23A, the cap retention means 800 comprises a dome-shaped flexible cap 114 that includes a first and second lever 118A, B with a circular detent, shoulder, or other similarly functioning retention means 116 all along the underside of the dome-shaped flexible cap 114 to engage the undercut 210 of a base wall 117 on the base 4. In an exemplary embodiment, the base wall 117 can be substantially circular and extend upwardly from the base 4. An upper surface of the base wall 117 can have the detent, shoulder, or other similarly functioning undercut means 210 to releasably capture the retention means 116 of the cap 114. A top surface of the undercut means 210 can be contoured or rounded, as can be the lower surface of the retention means 116, such that when contacting each other, each can be displaced slightly and slide over one another.

In an exemplary operation, the cap 114 can be pressed downward on the base 4 until the undercut means 210 is captured by the retention means 116. When the user then pushes on the first and second lever 118A, B along the force arrows A, B, the retention means 116 moves away from the undercut 210 of base wall 117 in the direction of arrows C, D allowing the user to remove the dome-shaped flexible cap 114. In the cap retention means 800 according to the seventh embodiment of the present invention, the first and second levers 118A, B, along with the portion of the dome-shaped flexible cap 114 between the point of contact of the levers 118A, B and the dome-shaped flexible cap 114, work as pivoting torsional springs. In doing so, a force pressing down, such as when the user pushes on the first and second lever 118A, B along the force arrows A, B, causes the dome-shaped flexible cap 114 to move away from the undercut 210, as shown in FIG. 23B. The first and second levers 118A, B also provide a means for gripping the cap 114.

Figure 24A:
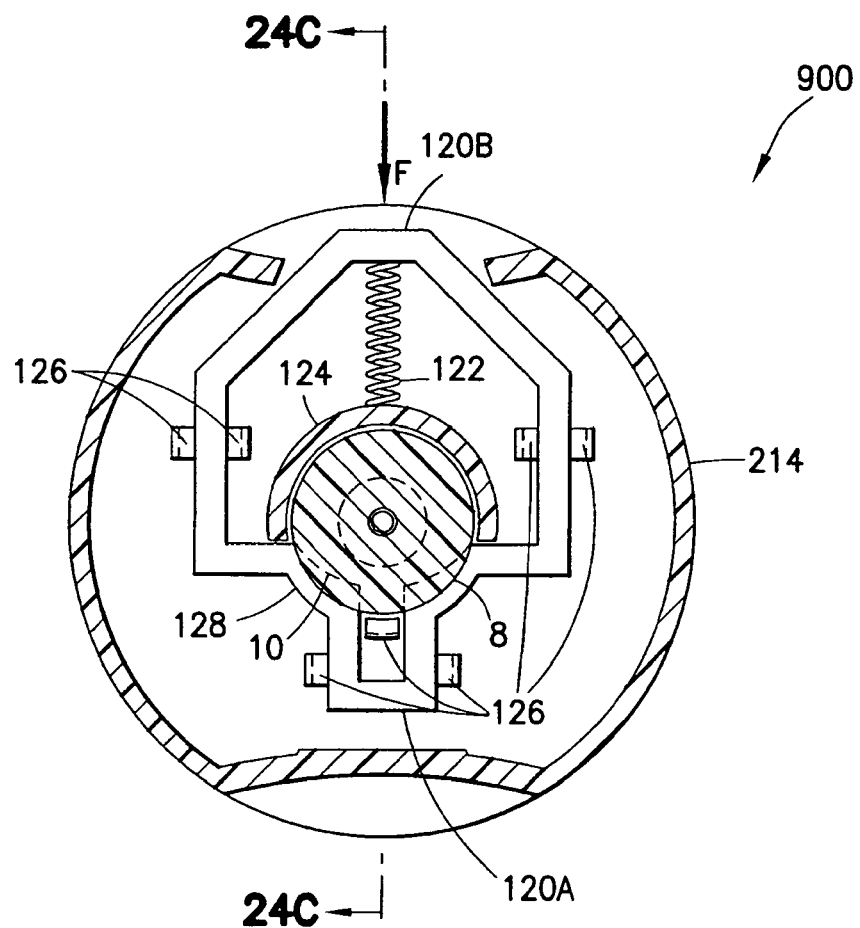
FIG. 24A is a bottom cross-sectional view of an exemplary latching mechanism to connect a tubing set to a connection port assembly in a latched condition according to an eighth embodiment of the present invention.

FIGS. 24A through 24D illustrate various top views of another exemplary cap retention means 900 according to an eighth embodiment of the present invention. In FIG. 24A, the cap retention means 900 comprises a rigid hoop 120, a spring 122, a first rigid hoop extension/retention member 124, a second rigid hoop extension/retention member 128, and guide members 126. The rigid hoop 120 comprises a contoured, rigid hoop to encircle the post 8, and comprises at least one guided side 120A and at least one user accessible side 120B. The user accessible side 120B is configured to allow the user to push the entire rigid hoop in the direction of arrow F of FIGS. 24A, B.

Elements of the rigid hoop 120 extending from the side 120B flare slightly to surround the post 8, and are guided by passage between a number of guide members 126. The side 120B is also urged in an opposite direction by the spring 122 captured between the side 120B and the first rigid hoop extension/retention member 124. On an opposite side of the post 8, the rigid hoop 120 is narrowed to provide at least one shoulder, or other similarly functioning second rigid hoop extension/retention member 128 to releasably capture a notch, detent or shoulder of the post 8 of the cap 214. The guided side 120A extends further, from the extension/retention member 128, and is guided by passage between a number of further guide members 126.

In such an arrangement, the spring 122 urges the rigid hoop 120 into a secured position, forcing the extension/retention member 128 to releasably capture the notch, detent or shoulder of the post 8 of the cap 214 as shown in FIG. 24A. By pushing the rigid hoop 120 inward, the extension/retention member 128 releases the notch, detent or shoulder of the post 8 of the cap 214 as shown in FIG. 24B.

For example, to place the cap 214 over the post 8 of the base 4, the user pushes the second side 120B of the rigid hoop 120 toward the first rigid hoop extension/retention member 124 against the force of the spring 122, slips the first side 120A of the rigid hoop 120 through the guide members 126, and then lowers the cap 214 onto the base 4. The user then releases the second side 120B of the rigid hoop 120, such that the second rigid hoop extension/retention means 128 become lodged under the undercut 10 of the post 8. The cap 214 is then locked onto the post 8 and base 4. FIG. 24A illustrates the latched condition of the cap retention means 900. FIG. 24C is a cross-sectional view of the cap retention means 900 as shown in FIG. 24A, and FIG. 24D is a cross-sectional view of the cap retention means 900 as shown in FIG. 24B.

Figure 24B:
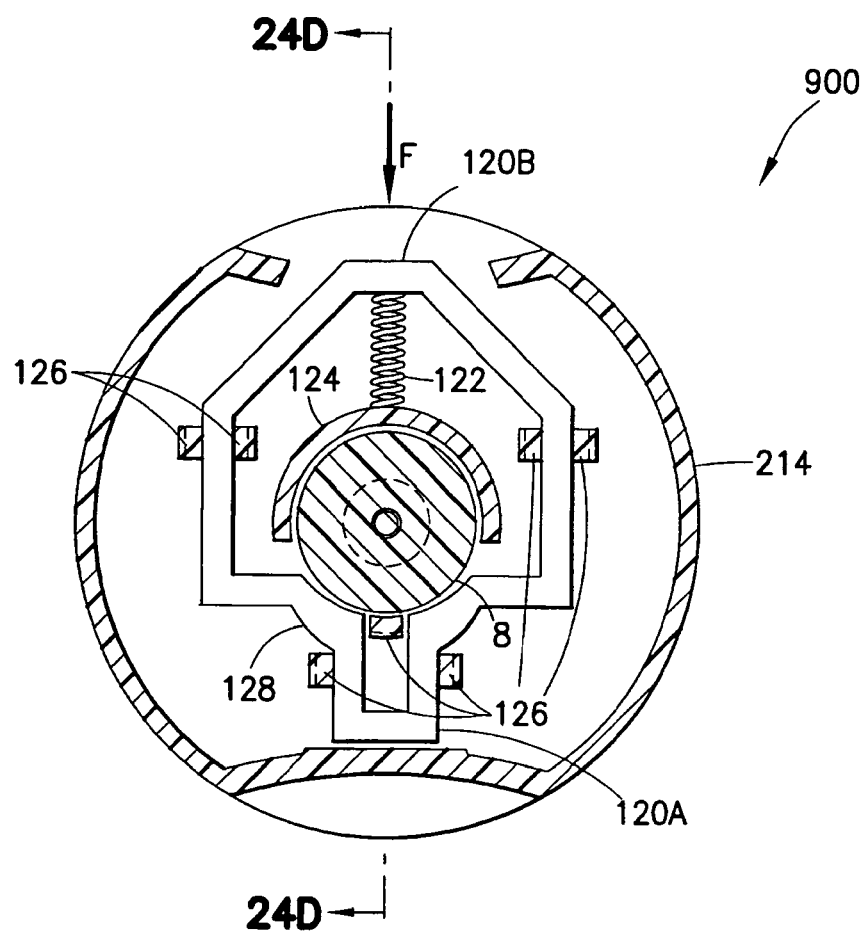
FIG. 24B is a bottom cross-sectional view of the latching mechanism shown in FIG. 24A to connect a tubing set to a connection port assembly in an unlatched condition in accordance with an embodiment of the present invention.
Figure 24C:
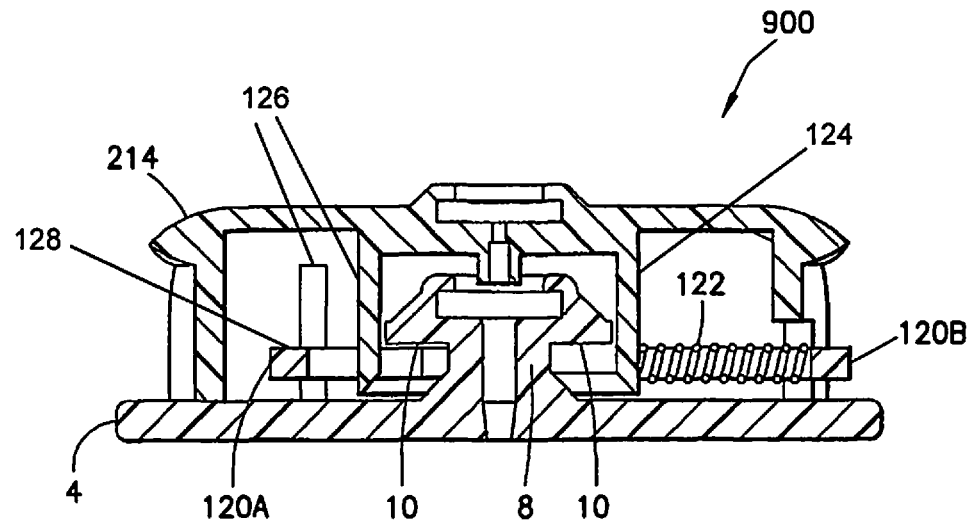
FIG. 24C is a cross-sectional view of the latching mechanism shown in FIG. 24A connecting the tubing set to the connection port assembly in a latched condition in accordance with an embodiment of the present invention.
Figure 24D:
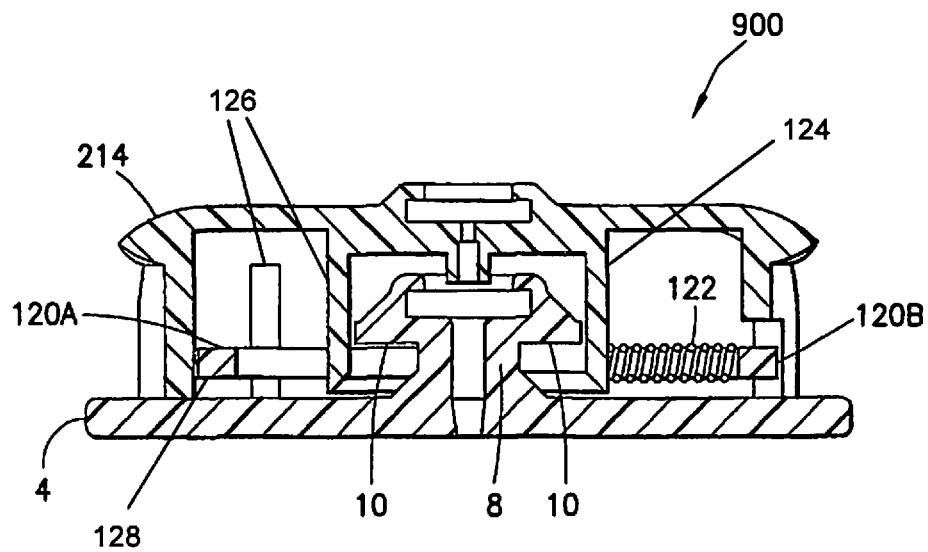
FIG. 24D is a cross-sectional view of the latching mechanism shown in FIG. 24A connecting the tubing set to the connection port assembly in an unlatched condition in accordance with an embodiment of the present invention.

To remove the cap 214, the user applies a force in the direction of the arrow F as shown in FIG. 24B. FIG. 24B illustrates the unlatched condition of the cap retention means 900. This pushes the second rigid hoop extension/retention member 128 out from under the undercut 10 of the post 8, and the user can then lift the cap 214. In alternative modifications to the cap retention means 900, the spring 122 can be made a separate part or can be integral to the rigid hoop 120. Further, the rigid hoop 120 can be fabricated to have other ribs for contacting the post 8 for stabilization, and can be continuous or can be open-sided like a "C" or "U" shape.

Figure 25A:
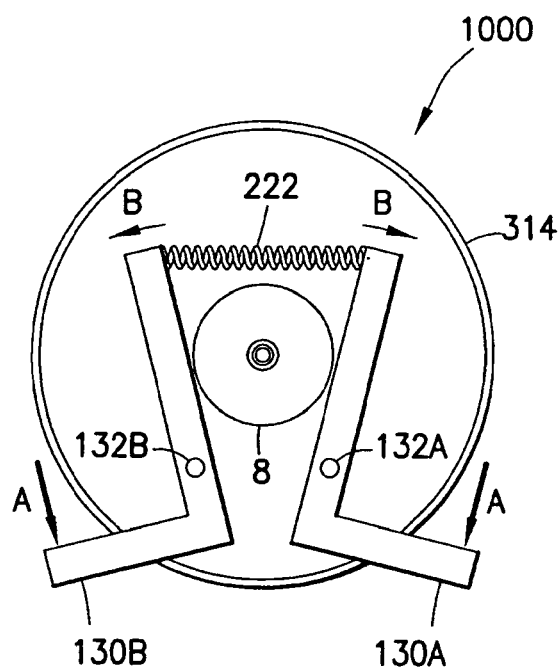
FIGS. 25A and 25B are bottom views of an exemplary latching mechanism to connect a tubing set to a connection port assembly according to a ninth embodiment of the present invention.
Figure 25B:
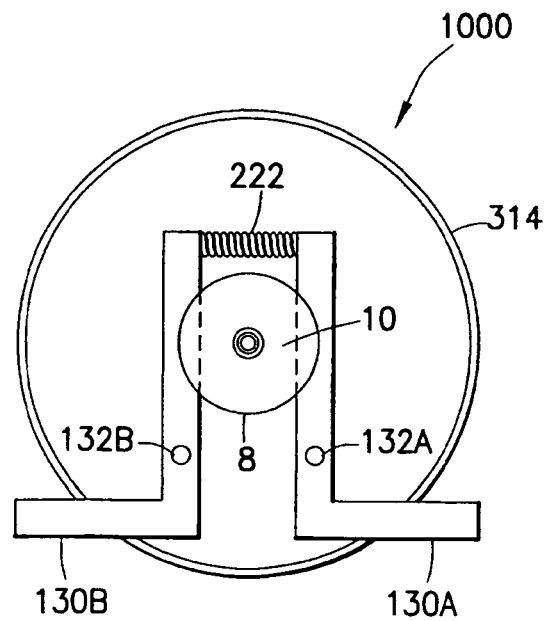

FIG. 25A is a bottom view of another exemplary cap retention means 1000 according to a ninth embodiment of the present invention in an unlatched condition, and FIG. 25B is a bottom view of the cap retention means 1000 in a latched condition. In FIG. 25A, the cap retention means 1000 comprises a first and second lever locking arm 130A, B and first and second pivots 132A, B. The first and second lever locking arms 130A, B each comprise an "L" shape and are linked at one end by a spring 222. The first and second lever locking arms 130A, B and the first and second pivots 132A, B are located on the underside of the cap 314 that interfaces with the post 8 of base 4. That is, each of the first and second lever locking arms 130A, B are rotatably secured to the cap 314 at the first and second pivots 132A, B. At opposite ends, at a point past the post 8, each of the first and second lever locking arms 130A, B are elastically secured to each other using the spring 222. In such an arrangement, the spring 222 urges the ends of the first and second lever locking arms 130A, B together into a secured position, forcing at least one portion of each locking arms 130A, B to releasably capture the notch, detent or shoulder of the post 8 of the cap 314 as shown in FIG. 25B. By pushing the locking arms 130A, B, in the direction of arrow A, the arms release the notch, detent or shoulder of the post 8 of the cap 314 as shown in FIG. 25A.

For example, to retain the cap 314 on the post 8 of base 4 (note that base 4 is not shown, only post 8), the user pushes the first and second lever locking arms 130A, B in the direction of the force arrows A as shown in FIG. 25A. The first and second lever locking arms 130A, B then rotate in the direction of arrows B, causing the spring 122 to expand. Eventually, the first and second lever locking arms 130A, B, are spaced far enough apart such that the post 8 can be fitted between them. This is the unlatched condition shown in FIG. 25A. Once the cap 314 is in place, the user relaxes the force applied at A and the first and second lever locking arms 130A, B, move to their relaxed position (as shown in FIG. 25B) under the undercut 10 of the post 8, thereby retaining the cap 314 onto the base 4. Various modifications can be made to the first and second lever locking arms 130A, B, including the shape and number of the first and second lever locking arms 130A, B. For example, in yet other exemplary embodiments, there can be only one lever locking arm, if desired, or more than those shown.

Figure 26A:
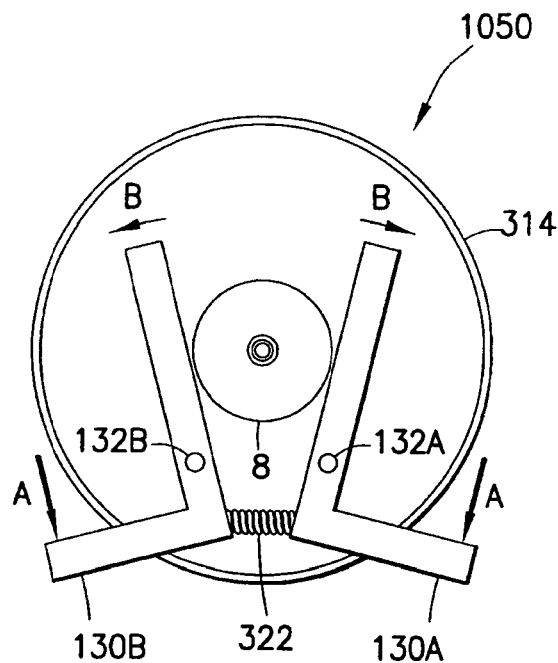
FIGS. 26A and 26B are bottom views of an alternative embodiment of the latching mechanism to connect a tubing set to a connection port assembly shown in FIGS. 25A and 25B in accordance with an embodiment of the present invention.
Figure 26B:
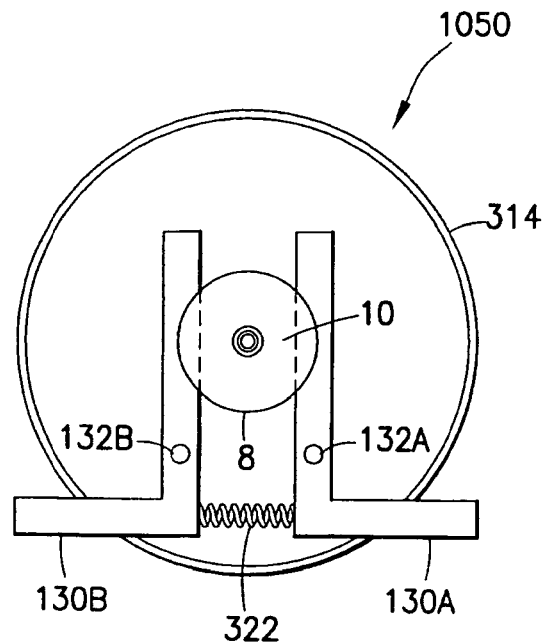

FIGS. 26A and 26B illustrate bottom views of an alternative embodiment of the latching mechanism to connect a tubing set to a connection post assembly shown in FIGS. 25A and 25B. FIGS. 26A and 26B, as with FIGS. 25A and 25B, show the bottom of the cap 314 and post 8 without including base 4 (to which post 8 would be attached) for purposes of clarity. The exemplary embodiment of FIGS. 26A and 26B are substantially as described above in regard to FIGS. 25A and 25B, except that the spring 322 is relocated to an opposite side of the post 8 to elastically connect the arms at a point at or near the right angle of each. However, in each embodiment, the spring can be configured to exert either an expansive force between connection points, or a contracting force between connection points. Accordingly, in doing so, the spring 322 urges the connection points of the arms apart and into a secured position.

For example, the cap retention means 1050 is shown in its relaxed state in FIG. 26B. The spring 322 pushes the first and second locking arms 130A, B about the first and second pivots 132 A, B such that a portion of the arms 130A, B latch under the undercut 10 of the post 8. To remove the cap 314 from the base 4, a force is applied in the direction of arrows A as shown in FIG. 26A, causing the first and second locking arms to swing in the direction of arrow B and out from undercut 10 of post 8. The cap 314 is then free to be removed, or become disassociated with the base 4.

Figure 27:
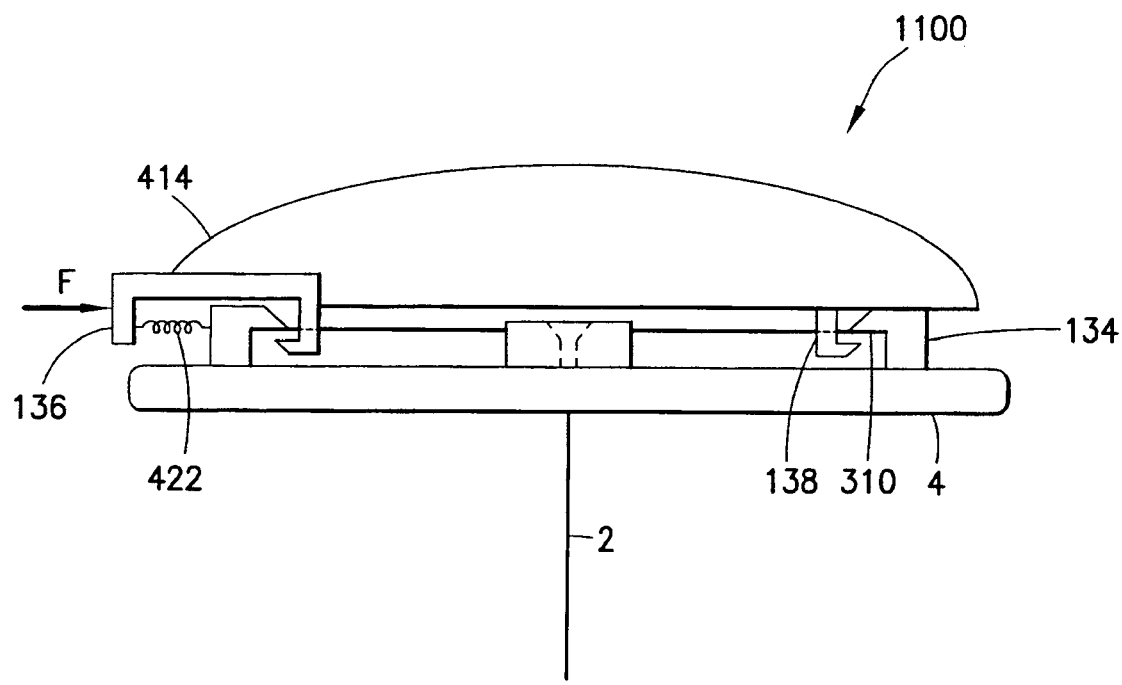
FIG. 27 is a side view of an exemplary latching mechanism to connect a tubing set to a connection port assembly of an exemplary infusion set according to a tenth embodiment of the present invention.

FIG. 27 illustrates a cross-sectional view of another exemplary cap retention means 1100 according to a tenth embodiment of the present invention. The cap retention means 1100 comprises the cap 414, spring 422, spring-urged retention member 136 and opposite facing lip 138. The infusion set in this embodiment of the present invention does not include the post 8 with an undercut. Instead, a cap retaining wall 134 is attached in a circular (or other shape) fashion around the point where the catheter 2 enters the body of the user, and the spring retention member 136 fits against it to secure the cap 414 to the base 4.

The cap retaining wall 134 can comprise an undercut 310 that interacts with both the spring retention means 136 and lip 138. In an exemplary embodiment, the cap retaining wall 134 can be substantially circular and extend upwardly from the base 4. An upper surface of the cap retaining wall 134 can have the detent, shoulder, or other similarly functioning undercut means 310 to releasably capture the spring-urged retention member 136 and lip 138 of the cap 414. A top surface of the undercut means 310 can be contoured, inclined or rounded, as can be the lower surface of spring-urged retention member 136 and lip 138, such that when contacting each other, each can be displaced slightly and slide over one another.

As seen in FIG. 27, the user places the cap 414, having the lip 138 extending downward therefrom, against the cap retaining wall 134, and the lip 138 which is attached to the cap 414, interfaces via one or more inclined surfaces between each, to thereby engage with the undercut 310 of the cap retaining wall 134. The user then presses the spring retention means 136 with a force applied in the direction of the arrow F, causing it, in this case, to move to the right. The user lowers the cap 414 fully down upon the cap retaining wall 134 and releases the spring retention means 136 causing it to lock into place under the undercut 310 of the cap 414. In doing so, the cap 414 can be located in any position on the base 4, so the cap retention means 1100 is not limited in any one particular direction, presuming the cap 414 and cap retaining wall 134 are circular. Other shapes can be used, and the directional qualities will depend upon the particular shape in use.

Figure 28:
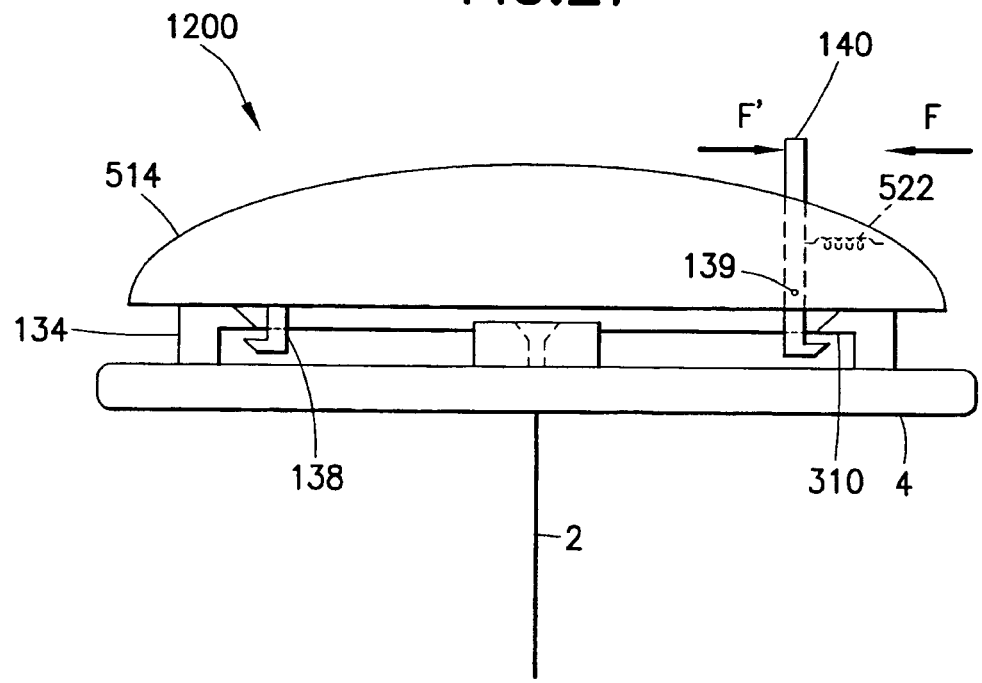
FIG. 28 is a side view of an exemplary latching mechanism to connect a tubing set to a connection port assembly of an exemplary infusion set according to an eleventh embodiment of the present invention.

FIG. 28 illustrates a side view of another exemplary cap retention means 1200 according to an eleventh embodiment of the present invention. The cap retention means 1200 comprises a cap 514, spring 522, and a lip 138. The infusion set in this embodiment of the present invention also does not include the post 8 with an undercut 10. Instead, as with the exemplary embodiment shown in FIG. 27, the cap retaining wall 134 is attached in a circular (or other shape) fashion around the point where the catheter 2 enters the body of the user, and the lip 138 fits against it to secure the cap 514 to the base 4.

As noted above, the cap retaining wall 134 can comprise an undercut 310 that interacts with a spring-urged retention lever 140. In an exemplary embodiment, the cap retaining wall 134 can be substantially circular and extend upwardly from the base 4. An upper surface of the cap retaining wall 134 can have the detent, shoulder, or other similarly functioning undercut means 310 to releasably capture the spring-urged retention lever 140 and lip 138 of the cap 514. A top surface of the undercut means 310 can be contoured, inclined or rounded, as can be the lower surface of spring-urged retention lever 140 and lip 138, such that when contacting each other, each can be displaced slightly and slide over one another.

As shown in FIG. 28, the user places the cap 514 against the cap retaining wall 134, and the lip 138, which is attached to the cap 514, interfaces with the undercut 310 of the cap retaining wall 134. The user then presses the spring retention lever 140 with a force applied in the direction of the arrow F, causing it, in this case, to move to the left against an elastic contracting force of the spring 522. In this exemplary embodiment, the lever moves back and forth without rotation (which is described in regard to another embodiment of the present invention below). The user lowers the cap 514 fully down upon the cap retaining wall 134 and releases the spring-urged retention lever 140, causing it to lock into place under the undercut 310-1-0 of the cap retaining wall 134. The spring retention lever 140 can lock into the undercut 310 at any location of the cap retaining wall 134 so the cap retention means 1200 is not limited in any one particular direction, presuming the cap 514 and cap retaining wall 134 are circular. Other shapes can be used, and the directional qualities will depend upon the particular shape in use.

The spring-urged retention lever 140 can further be provided with the pivot 139 about which the lever 140 can be rotated. Accordingly, in this exemplary embodiment, the user is required to apply the force in the direction of arrow F' to release or attach the cap 514 to the base 4. The spring retention lever 140 pivots about the pivot 139, as resisted by the force of the spring 522, so that while the top moves to the right, the bottom moves to the left.

The present invention has been described with reference to exemplary embodiments thereof. However, it will be readily apparent to those skilled in the art that it is possible to embody the invention in specific forms other than those of the exemplary embodiments described above. This may be done without departing from the spirit of the invention as defined in the appended claims and equivalents thereof. The exemplary embodiments are merely illustrative and should not be considered restrictive in any way.

The invention claimed is:

1. An infusion set, comprising:
   a base having a post; and
   a cap having:
   an opening having an interior space for receiving the post;
   a cannula extending into the interior space of the opening; and
   a deflectable coupling member comprising a user-depressible element angularly connected to an outwardly bending flexible member, the deflectable coupling member having a closed shape surrounding the cannula;
   wherein the outwardly bending flexible member is configured to releasably engage the post in the interior space when the user-depressible element is in a free state to couple the cap to the base in a desired rotational position about the post; and
   when the user-depressible element is in a depressed state, at least a portion of the outwardly bending flexible member extends further outwardly out of the interior space to disengage the post.

2. An apparatus as claimed in claim 1, wherein the post comprises an inclined upper surface configured to align with and receive the deflectable coupling member of the cap.

3. An apparatus as claimed in claim 2, wherein the outwardly bending flexible member comprises an inclined lower surface configured to be displaced by engagement with the inclined upper surface of the post, and upon release by the inclined upper surface of the post, engage the post in any one of a 360 degree rotational position about the post.

4. An apparatus as claimed in claim 1, wherein the post comprises a plurality of ribs upon an outer circumference.

5. An apparatus as claimed in claim 4, wherein the deflectable coupling member of the cap comprises a plurality of ribs upon a portion of the outwardly bending flexible member configured to engage the plurality of ribs upon a portion of the outer circumference of the post.

6. An apparatus as claimed in claim 5, wherein the deflectable coupling member of the cap is configured to deflect between,
at least one position wherein the deflectable coupling member of the cap releases the post of the base,
at least one position wherein the deflectable coupling member of the cap engages the post to secure the base and cap together while permitting rotation, and
at least one position wherein the deflectable coupling member of the cap engages the post to secure the base and cap together and engage the plurality of ribs of the deflectable coupling member with the plurality of ribs upon the post to resist rotation.

7. An apparatus as claimed in claim 1, further comprising an insertion needle comprising at least one opening adjacent to an input of the infusion set to prime the set.

8. An apparatus as claimed in claim 1, further comprising:
a septum; and
a septum fixing wedge to secure the septum to the base.

9. An apparatus as claimed in claim 1, wherein the base comprises at least one window for viewing an insertion site beneath the base.

10. An infusion set as claimed in claim 1, wherein the outwardly bending flexible member further comprises a relief to target and ease bending of the deflectable coupling member.

11. An infusion set comprising:
a base having a post;
a cap having:
a rotatable coupling member;
a cannula;
an alignment opening surrounding the cannula; and
an interlocking opening; and
a mechanism to secure the cap to the base, said mechanism comprising a user-depressible element configured to extend through the interlocking opening;
wherein the alignment opening aligns with and slidably receives the post;
wherein the cap angularly rotates about the rotatable coupling member toward the base for coupling and the cap angularly rotates about the rotatable coupling member away from the base for decoupling; and
wherein the user-depressible element is integral with the base to form a monolithic structure.

12. An apparatus as claimed in claim 11, further comprising an infusion set tube extending from the rotatable coupling member parallel to the base.

13. An apparatus as claimed in claim 11, further comprising an infusion set tube extending from the cap perpendicular to the base.

14. An apparatus as claimed in claim 11, wherein the user-depressible element secures the cap at a point opposite to the rotatable coupling member.

15. An apparatus as claimed in claim 11, wherein the base comprises at least one window for viewing an insertion site beneath the base.

16. A cap for an infusion set, comprising:
an opening for receiving a post of an infusion set base; and
a coupling member disposed in the opening;
wherein the coupling member is configured to selectively extend into and out of the opening to substantially encircle the post of the infusion set base, said coupling member having:
a user deflectable side extending from said opening to an outside of the cap, and
at least one side configured to deflect in response to movement of the user deflectable side,
the at least one side having an extended portion that is configured to deflect in response to the movement of the user deflectable side such that the extended portion engages the post of the infusion set base when a proximal end of the user deflectable side is disposed outside the cap, and the extended portion disengages the post of the infusion set base when the proximal end of the user deflectable side extends into and is disposed inside the cap.

17. A cap for an infusion set as claimed in claim 16, wherein the extended portion of the at least one side comprises a curved surface, wherein the curved surface deflects in response to the movement of the user deflectable side to engage and disengage the post.

18. A cap for an infusion set as claimed in claim 16, wherein the coupling member further comprises:
the user deflectable side configured to slidably move relative to the post; and
the extended portion configured to engage the post in a first slidable position and release the post in a second slidable position.

19. A cap for an infusion set as claimed in claim 18, further comprising a spring member to urge the user deflectable side into the first slidable position.

20. An infusion set comprising:
a cap having
a deflectable coupling member disposed on an underside of the cap, said deflectable coupling member comprising at least one user-depressible lever extending outwardly from said underside of said cap, the at least one user-depressible lever moving with the deflectable coupling member in a same direction; and
a base comprising at least one cap retaining wall with at least one undercut surface disposed below the at least one cap retaining wall,
wherein the deflectable coupling member is configured to releasably couple the cap to the base in a desired rotational position.

21. An apparatus as claimed in claim 20, wherein the deflectable coupling member engages and disengages the at least one undercut surface of the at least one cap retaining wall.

* * * * *